United States Patent
Quispe et al.

(10) Patent No.: US 11,995,829 B2
(45) Date of Patent: *May 28, 2024

(54) 2D SHEAR WAVE DISPERSION IMAGING USING A REVERBERANT SHEAR WAVE FIELD

(71) Applicant: UNIVERSITY OF ROCHESTER, Rochester, NY (US)

(72) Inventors: Juvenal Ormachea Quispe, Rochester, NY (US); Kevin J. Parker, Rochester, NY (US); Jose Fernando Zvietcovich Zegarra, Rochester, NY (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/151,114

(22) Filed: Jan. 6, 2023

(65) Prior Publication Data

US 2023/0154001 A1    May 18, 2023

Related U.S. Application Data

(63) Continuation of application No. 16/903,569, filed on Jun. 17, 2020, now Pat. No. 11,562,483.
(Continued)

(51) Int. Cl.
*G06K 9/00* (2022.01)
*A61B 8/00* (2006.01)
(Continued)

(52) U.S. Cl.
CPC .......... *G06T 7/0012* (2013.01); *A61B 8/4444* (2013.01); *A61B 8/4483* (2013.01);
(Continued)

(58) Field of Classification Search
CPC ............. G06K 9/00; A61K 35/12; A61B 8/00
(Continued)

(56) References Cited

U.S. PATENT DOCUMENTS

| | | | | |
|---|---|---|---|---|
| 2011/0063950 | A1* | 3/2011 | Greenleaf | G01S 7/52038 367/87 |
| 2011/0263978 | A1* | 10/2011 | Chen | A61B 8/485 600/438 |

(Continued)

OTHER PUBLICATIONS

Carolina Amador et al., Shearwave Dispersion Ultrasound Vibrometry (SDUV) on Swine Kidney, IEEE Transactions on UL Trasonics, Ferroelectrics, and Frequency Control, vol. 58, No. 12, Dec. 2011, pp. 2608-2619.

(Continued)

*Primary Examiner* — Seyed H Azarian
(74) *Attorney, Agent, or Firm* — Ping Wang; Rimon Law

(57) ABSTRACT

Within the field of elastography, a new approach analyzes the limiting case of shear waves established as a reverberant field. In this framework, it is assumed that a distribution of shear waves exists, oriented across all directions in 3D (e.g. 2D space+time). The simultaneous multi-frequency application of reverberant shear wave fields can be accomplished by applying an array of external sources that can be excited by multiple frequencies within a bandwidth, for example 50, 100, 150, . . . 500 Hz, all contributing to the shear wave field produced in the liver or other target organ. This enables the analysis of the dispersion of shear wave speed as it increases with frequency, indicating the viscoelastic and lossy nature of the tissue under study. Furthermore, dispersion images can be created and displayed alongside the shear wave speed images. Studies on breast and liver tissues using the multi-frequency reverberant shear wave technique, employing frequencies up to 700 Hz in breast tissue, and robust reverberant patterns of shear waves across the entire liver (Continued)

and kidney in obese patients are reported. Dispersion images are shown to have contrast between tissue types and with quantitative values that align with previous studies.

20 Claims, 12 Drawing Sheets

Related U.S. Application Data

(60) Provisional application No. 62/867,382, filed on Jun. 27, 2019.

(51) Int. Cl.
*A61B 8/08* (2006.01)
*G06T 7/00* (2017.01)

(52) U.S. Cl.
CPC .............. *A61B 8/469* (2013.01); *A61B 8/485* (2013.01); *G06T 2207/10028* (2013.01); *G06T 2207/10088* (2013.01); *G06T 2207/10101* (2013.01); *G06T 2207/10132* (2013.01); *G06T 2207/30056* (2013.01); *G06T 2207/30068* (2013.01)

(58) Field of Classification Search
USPC ........ 382/100, 103, 106–107, 128–132, 154, 382/162, 168, 173, 181, 191, 194, 224, 382/254, 274, 276, 285, 291, 305; 367/87; 378/4, 21; 600/437, 438
See application file for complete search history.

(56) References Cited

U.S. PATENT DOCUMENTS

| | | | |
|---|---|---|---|
| 2014/0316267 A1* | 10/2014 | Barry ................... | A61B 8/4483 600/438 |
| 2016/0035548 A1 | 2/2016 | Brown et al. | |
| 2018/0156902 A1* | 6/2018 | Mcgough ............ | G01S 15/8915 |
| 2019/0029649 A1* | 1/2019 | Tanigawa ............. | A61B 8/5246 |
| 2021/0018606 A1* | 1/2021 | McCaw ................ | G01N 29/34 |

OTHER PUBLICATIONS

Richard G. Barr, Elastography in clinical practice Radiol Clin North Arn, vol. 52, pp. 1145-1162, 2014.
Richard G. Barr et al., WFUMB Guidelines and Recommendations for Clinical Use of Ultrasound Elastography: Part 2: Breast, Ultrasound in Med. & Biol., vol. 41, No. 5, pp. 1148-1160, 2015.
Christoper T, Barry et aL, Mouse Liver Dispersion for the Diagnosis of Early-Stage Fatty Liver Disease: A 70-Sample Study, Ultrasound in Med. & Biol., vol. 40, No. 4, pp. 704-713, 2014.
Christoper T, Barry et al., Shear Wave Dispersion in Lean Versus Steatotic Rat Liver, 2015 by the American Institute of Ultrasound in Medicine, J Ultrasound Med 2015; 34:1123-1129.
Samuel Calle et al., Shear wave velocity dispersion analysis in placenta using 2-D transient Elastography, Journal of Applied Physics 123, pp. 234902-234902-9, (2018).
Deniz Cebi Olgun et al., Use of sllear wave elastography to differentiate benign and malignant breast lesions, Diagn Interv Radiol 2014; 20: pp. 239-244.
Jung Min Chang et al., Clinical application of shear wave elastography (SWE) in t?1e diagnosis of benign and malignant breast diseases, Breast Cancer Res Treat (2011) vol. 129 pp. 89-97.
Thomas Deffieux et al., Shear Wave Spectroscopy for In Vivo Quantification of Human Soft Tissues Visco-Elasticity, IEEE Transactions on Medical Imaging, vol. 28, No. 3, Mar. 2009, pp. 313-322.
M. Elseedawy et al., Factors influencing the stiffness of fibroadenomas at shear wave elastography, Clinical Radiology vol. 71 (2016) pp. 92-95.

Giovanna Ferraioli et al., WFUMB Guidelines and Recommendations for Clinical Use of Ultrasound Elastography: Part 3: Liver, Ultrasound in Med. & Biol., vol. 41, No. 5, pp. 1161-1179, 2015.
Christian A. Hudert et al., US Time-Harmonic Elastography: Detection of Liver Fibrosis in Adolescents with Extreme Obesity with Nonalcoholic Fatty Liver Disease Radiology 2018, vol. 288, pp. 99-106.
Viksit Kumar et al., Viscoelastic parameters as discriminators of breast masses: Initial human study results, PLoS ONE 13 (10): e0205717, 2018, pp. 1-15.
Thanasis Loupas et al., An Axial Velocity Estimator for Ultrasound Blood Flow Imaging, Based on a Full Evaluation of the Doppler Equation by Means of a Two-Dimensional Autocorrelation Approall, IEEE Transactions on Ultrasonics, Ferroelectrics, and Frequency Control, vol. 42, No. 4, Jul. 1995, pp. 672-688.
Marie Muller et al., Quantitative Viscoelasticity Mapping of Human Liver Using Supersonic Shear Imaging: Preliminary In Vivo Feasability Study, Ultrasound in Med. & Biol., vol. 35, No. 2, 2009, pp. 219-229.
Kathryn R. Nightingale et al., Derivation and Analysis of Viscoelastic Propeliies in Human Liver: Impact of Frequency on Fibrosis and Steatosis Staging, IEEE Transactions on Ultrasonics, Ferroelectrics, and Frequency Control, vol. 62, No. 1, Jan. 2015, pp. 165-175.
Juvenal Ormachea et al., Shearwa.Ve Speed Estimation Using Reverberant Shearwa.Ve Fields: Implementation and Feasibility Studies, Ultrasound in Med. & Biol., vol. 44, No. 5, 2018, pp. 963-977.
Mark Palmeri et al., RSNA QIBA Ultrasound Sllear Wave Speed Pllase li Phantom Study in Viscoelastic Media, IEEE International Ultrasonics Symposium Proceedings, 978-1-4 799-8182-3i15/$31 .00 Å © 2015 IEEE.
Kevin J. Parker et al, Imaging the elastic properties of tissue: tile 20 year perspective, Phys. Med. Biol. 56 (2011) pp. R1-R29.
Kevin J. Parker et al, What Dowe Knowabout Shear Wave Dispersion in Normal and Steatotic Livers?, Ultrasound in Med. & Biol., vol. 41, No. 5, 2015, pp. 1481-1487.
Kevin J. Parker, et al., Shear wave dispersion behaviors of soft, vascularized tissues from tile microcl1annel flow model, Pllys. Med. Biol. 61 (2016) pp. 4890-4903.
Kevin J. Parker, et al. Reverberant sllear wave fields and estimation of tissue properties, Phys. Med. Biol. 62 (2017) pp. 1046-1061.
Kevin J. Parker et al., Group versus Ptiase Velocity Shear Waves in Soft Tissues, Ultrasonic Imaging 2018, vol. 40(6). The AutL1or(s) 2018, pp. 343-356.
Ned C. Rouze et al., Characterization of Viscoelastic Materials Using Group Shear Wave Speeds, IEEE Transactions on Ultrasonics, Ferroelectrics, and Frequency Control, vol. 65, No. 5, May 2018. pp. 780-794.
Tsuyoshi Shiina et al., WFUMB Guidelines and Recommendations for Clinical Use of Ultrasound Elastography: Part 1: Basic Principles and Terminology. Ultrasound in Med. & Biol., vol. 41, No. 5, 2015, pp. 1126-1147.
Emmanuel G. Simon et al., Measurement of s?1ear wave speed dispersion in the placenta by transient elastography: A preliminary ex vivo study, PLoS ONE 13(4): e0194309, 2018, pp. 1-20.
Ralph Sinkus et al., MR Elastography of Breast Lesions: Understanding the Solid/Liquid Duality Can Improve ttle Specificity of Contrast-Enhanced MR Mammography, Magnetic Resonance in Medicine 58, (2007), 1 pp. 135-1144.
Mickael, Tanter et al., Quantitative Assessment of Breast Lesion Viscoelasticity: Initial Clinical Results Using Supersonic Shear Imaging, Ultrasound in Med. & Biol., vol. 34, No. 9, 2008, pp. 1373-1386.
Heiko Tzscheatzsch et al., Mul Ti Frequency Time-Harmonic Elastography for the Measurement of Liver Viscoelasticity in Large Tissue Windows, Ultrasound in Med. & Biol., vol. 41, No. 3,2015, pp. 724-733.
Matthew W. Urban et al., Comparison of Shear Velocity Dispersion in Viscoelastic Phantoms Measured by Ultrasound based Shear Wave Elastography and Magnetic Resonance Elastography, Department of Radiology, Mayo Clinic, Rochester, MN, USA, 4 pages.
Wei Zhang, Estimation of shear modulus in media with power law characteristics, Ultrasonics 64 (2016) pp. 170-176.

(56) References Cited

OTHER PUBLICATIONS

Fernando Zvietcovich, et al., Reverberant 3D Optical Coherence Elastography (REV3D-OCE): A Novel Method for the 3D Elastic Mapping of Layers in Cornea, University of Rochester, Rochester, NY, USA, 2Suranaree University of Technology, Nakhon Ratchasima, Thailand, 1 page.

* cited by examiner

Fig. 3 (CIRS Breast Phantom)

Fig. 4 (CIRS Viscoelastic Phantom)

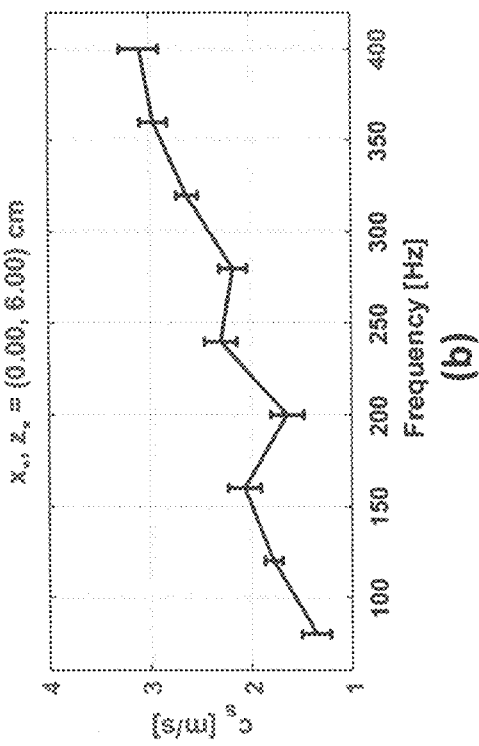
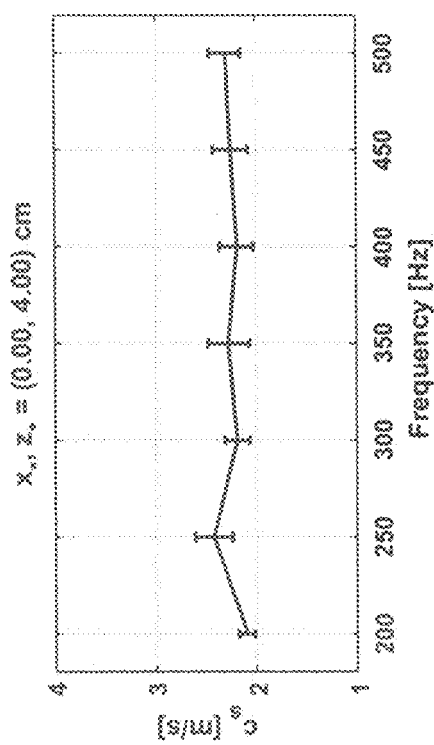
Fig. 5

Fig. 6 (Liver Obese Case 2)

Fig. 7 (Liver Obese Case 3)

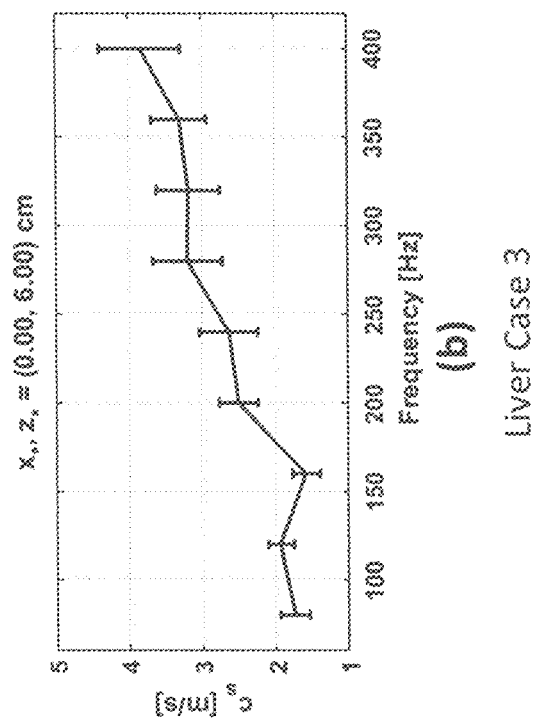
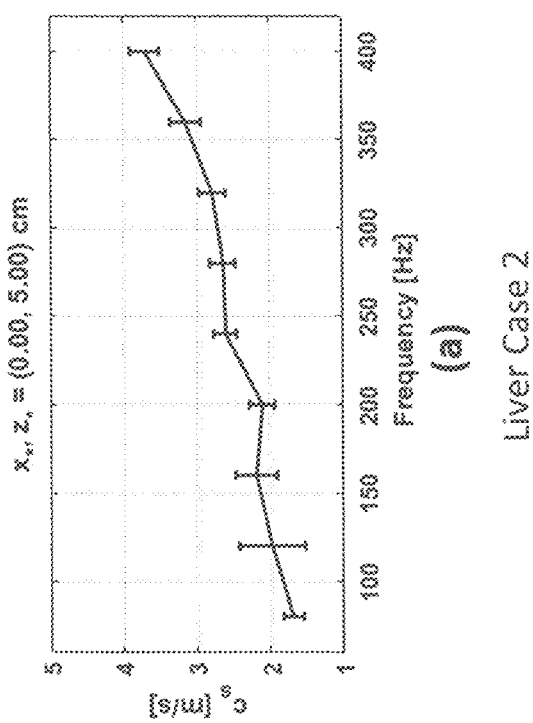
Fig. 8

Fig. 9 (Breast Fibroadenoma Case)

Fig. 10 (Dense Breast Tissue Case)

Fig. 11
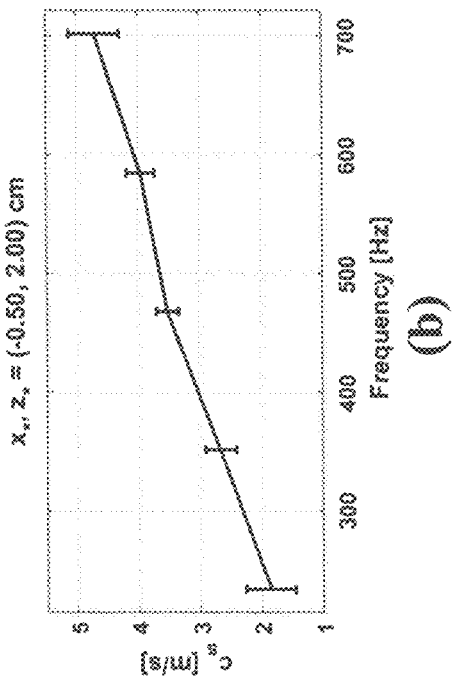
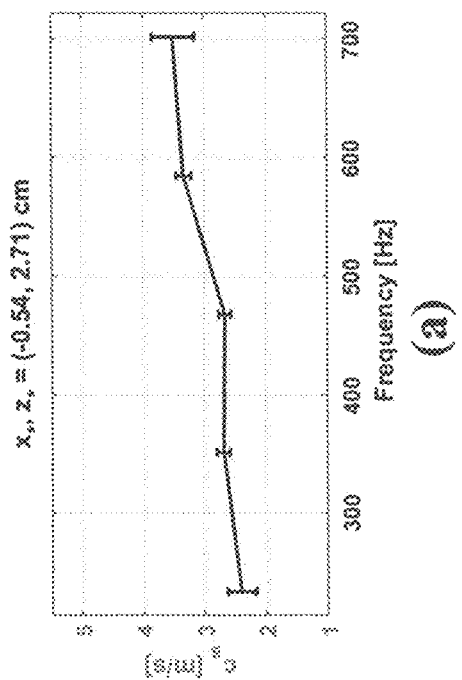

2D SHEAR WAVE DISPERSION IMAGING USING A REVERBERANT SHEAR WAVE FIELD

This application incorporates by reference and is a Continuation Application of U.S. application Ser. No. 16/903,569, filed Jun. 17, 2020 which claims the benefit to U.S. provisional patent application Ser. No. 62/867,382 filed on Jun. 27, 2019, which is incorporated herein by reference.

FIELD

This patent specification relates to medical systems and methods for imaging patients' internal tissue for screening and/or diagnostic purposes and to estimating and displaying elastographic properties of internal tissue on a pixel-by-pixel basis.

BACKGROUND

This patent application cites publications that are listed at the end of the Detailed Description and are identified by author and date throughout the discussion below. This patent application incorporates by reference each of said publications and U.S. patent application Ser. No. 16/346,327 filed on Apr. 30, 2019 and International Application PCT/US2017/059875 filed Nov. 3, 2017 (published as WO 2018/093584 A1 and claiming the benefit of U.S. Provisional Patent Application No. 62/422,765 filed Nov. 16, 2016).

Elastography is a medical imaging modality that estimates biomechanical properties of tissues. Several groups have proposed ways to measure shear wave speed (SWS), shear modulus, and other mechanical parameters to correlate them with elastic tissue properties (Parker et al., 2010; Barr, 2014; Shiina et al., 2015). Soft tissues have viscoelastic properties and exhibit a frequency-dependent SWS, a phenomenon called dispersion. Generally, higher frequency shear wave components propagate faster than lower frequency components, and this dispersion can be measured over some bandwidth (Parker et al., 2015).

The Radiological Society of North America Quantitative Imaging Biomarkers Alliance (RSNA/QIBA) (Palmeri et al., 2015) reported attempting to obtain a better characterization of various calibrated phantoms across different imaging systems by measuring the SWS and linear dispersion at a reference frequency of 200 Hz. Urban et al. (2017) reported measuring the SWS dispersion over a wide range of frequencies (60-600 Hz) in three different viscoelastic phantoms; and that the dispersion measurements helped to better differentiate the viscoelastic properties of these materials. Rouze et al. (2018) reported estimating viscoelastic properties in calibrated phantoms by creating multiple lookup tables based on pair values of group SWS and dispersion at 200 Hz. In liver tissue, (Barry et al., 2014; Barry et al., 2015) reported measuring linear dispersion in 70 ex vivo lean and steatotic rat livers using crawling wave sonoelastography. These studies showed elevated linear dispersion in obese rats. An extended technical note reported by Parker et al. (2015) summarized the importance of measuring dispersion in normal and steatotic livers in different studies using shear wave elastography (SWE). More recently, Hudert et al. (2018) and Tzschatzsch et al. (2015) reported measuring SWS and dispersion in in vivo liver tissue and correlating them with different grades of fibrosis using an external speaker that vibrates at multiple frequencies to generate shear waves. The vibration frequency ($f_v$) range was 30 to 60 Hz; however, it has been shown that dispersion is frequency dependent, and is high at lower frequency ranges compared to higher frequencies (Parker et al., 2018). In placenta tissue, Parker et al. (2016) used the single tracking location acoustic radiation force technique to measure the SWS in ex vivo perfused samples and evaluated the SWS dispersion with a microchannel flow model. This study showed that dispersion increases after the administration of a vasoconstrictor agent compared with normal perfused placenta tissue. Simon et al. (2018) and Callé et al. (2018) reported analyzing the SWS dispersion using transient elastography and a rheological model in 10 and 20 ex vivo normal placenta tissues, respectively. Based on their results, dispersion may help to identify differences between placental structures. SWS dispersion was also related to the viscosity properties in kidney tissue. Amador et al. (2011) reported applying shear wave dispersion ultrasound vibrometry (SDUV) over a bandwidth of 50 to 500 Hz in 8 excised swine kidneys and found a statistical difference between shear elasticity and shear viscosity. Additionally, they reported measuring an increase in dispersion of more than 30% after immersion in 10% formaldehyde. This study showed that the inhomogeneous structure of kidney can be better characterized by measuring both SWS and dispersion. SDUV reportedly has been used to estimate the viscoelastic properties in breast tissue over a frequency range of 50 to 400 Hz (Kumar et al., 2018). Although SWS dispersion was not directly measured in this study, the viscoelastic properties of normal breast tissue and benign and malignant masses were obtained by fitting the SWS versus frequency curve with a Voigt model. Similarly, a previous study by Tanter et al. (2008), reportedly measured the SWS in different breast lesions and showed a dispersion curve for the breast parenchyma over 100 to 400 Hz. This SWS frequency dependence curve illustrated why they were reporting higher SWS values compared to other studies that used lower mechanical frequencies and left open the question whether higher frequencies could provide better differentiation between benign and malignant breast lesions. As observed in these different studies, SWE (shear wave elastography) may help obtain a better characterization of the biomechanical properties of tissues by additionally measuring the SWS dispersion.

SUMMARY OF THE DISCLOSURE

According to some embodiments, a system for estimating and displaying linear dispersion slope (LDS) and power law coefficient (PLC) values on a pixel-by-pixel basis for a corresponding internal region of a subject comprises: a source of shear waves propagating in multiple directions, said source being configured to concurrently induce shear waves at respective different vibration frequencies in a region of interest (ROI) in the subject; an imaging system measuring displacement as a function of time of respective voxels in said ROI in the presence of said induced shear waves; a computer processor configured to apply computer algorithms to said displacements and account for said vibration frequencies to calculate respective shear wave speeds in said ROI and to further calculate a respective LDS and PLC value for each pixel in an array of pixels corresponding to respective voxels in said ROI; and a computer display configured to selectively display said arrays of LDS and PLC pixel values.

According to some embodiments: the processor can be further configured to account in said computer algorithms for effects of attenuation (alpha) of said shear waves as they propagate in said ROI; these effects of attenuation can be accounted for by including a complex wavenumber in said calculating of LDS and PLC values, wherein both a real part and a complex part of said wavenumber contribute to assessing said pixel values; the source of shear waves can comprise a patient bed with plural sources of vibration frequencies embedded in an active region of said bed, wherein said plural sources are configured to vibrate concurrently; the imaging system can comprise an ultrasound scanner and an imaging ultrasound transducer; the scanner and transducer can be configured to measure said displacements to a depth in the patient of at least 10 cm, and to measure said displacement in a patient's liver or in the patient's breast; the imaging system can be an MRI scanner or an OCT (Optical Coherence Tomography) scanner rather than an ultrasound scanner; the vibration frequencies can include at least frequencies up to 700 Hz, and can include frequencies in the range of 60-702 Hz; and the source can be configured to step said vibration frequencies is selected steps within a selected range of frequencies.

According to some embodiments, a method of estimating and displaying linear dispersion slope (LDS) and power law coefficient (PLC) values on a pixel-by-pixel basis for a corresponding internal region of a subject comprises: concurrently inducing plural shear waves at respective different vibration frequencies in a region of interest (ROI) in the subject; measuring displacement as a function of time of respective voxels in said ROI in the presence of said induced shear waves; applying computer algorithms to said displacements and account for said vibration frequencies to calculate respective shear wave speeds in said ROI and to further calculate a respective LDS and PLC value for each pixel in an array of pixels corresponding to respective voxels in said ROI; and displaying said arrays of LDS and PLC pixel values.

According to some embodiments, the method can comprise: including accounting in said computer algorithms for effects of attenuation of said shear waves as they propagate in said ROI, by using a complex wavenumber in said calculating of LDS and PLC values, wherein both a real part and a complex part of said wavenumber contribute to assessing said pixel values; and the measuring can comprise using an ultrasound scanner and an imaging ultrasound transducer, to measure said displacement in a patient's liver, to a depth in the patient of at least 10 cm.

According to some embodiments, a system for mapping linear dispersion slope (LDS) values on a pixel-by-pixel basis for a corresponding internal region of a subject comprises: a source of shear waves propagating in multiple directions, said source being configured to concurrently induce shear waves at respective different vibration frequencies in a region of interest (ROI) in the subject; an imaging system measuring displacement as a function of time of respective voxels in said ROI in the presence of said induced shear waves; a computer processor configured to apply computer algorithms to said displacements and take into account said vibration frequencies to calculate respective shear wave speeds in said ROI and to further calculate a respective LDS value for each pixel in an array of pixels corresponding to respective voxels in said ROI; and a computer display configured to selectively display said arrays of LDS pixel values. The computer processor can be further configured to apply computer algorithms to said displacements and account for said vibration frequencies to calculate a power law coefficient (PLC) value for each of said pixels.

According to some embodiments, a system for estimating and displaying linear dispersion slope (LDS) and power law coefficient (PLC) values on a pixel-by-pixel basis for an internal region of a subject comprises: a source of a plurality of shear waves configured to concurrently induce shear waves at respective different vibration frequencies in a region of interest (ROI) in the subject; an imaging system configured to measure displacements as a function of time of respective voxels in said ROI in the presence of said induced shear waves; a computer processor configured to apply computer algorithms to said displacements and account for said vibration frequencies to calculate respective shear wave speeds in said ROI and to further calculate a respective LDS and PLC value for each pixel in an array of pixels corresponding to respective voxels in said ROI; and a computer display configured to selectively display said arrays of LDS and PLC pixel values. The source of shear waves can comprise a generator of a multi-tone signal with randomized phases that produces a waveform with an approximately uniform envelope.

According to some embodiments, a system for estimating and displaying linear dispersion slope (LDS) and power law coefficient (PLC) values and shear wave attenuation (alpha) values on a pixel-by-pixel basis for an internal region of a subject comprises: a source of a plurality of shear waves configured to concurrently induce shear waves at respective different vibration frequencies in a region of interest (ROT) in the subject; an imaging system measuring displacements as a function of time of respective voxels in said ROI in the presence of said induced shear waves; a computer processor configured to apply computer algorithms to said displacements and account for said vibration frequencies to calculate respective shear wave speeds in said ROI and to further calculate a respective LDS and PLC and alpha value for each pixel in an array of pixels corresponding to respective voxels in said ROI; and a computer display configured to selectively display said arrays of LDS and PLC pixel values. The computer processor can be configured to calculate said alpha values from real and imaginary parts of a complex autocorrelation function of said displacements.

According to some embodiments, a method of imaging linear dispersion slope (LDS) and power law coefficient (PLC) values on a pixel-by-pixel basis for an internal region of a subject comprises: concurrently inducing shear waves at respective different vibration frequencies in a region of interest (ROI) in the subject; measuring displacements as a function of time of respective voxels in said ROI in the presence of said induced shear waves; applying computer algorithms to said displacements and accounting for said vibration frequencies to calculate respective shear wave speeds in said ROI and to further calculate a respective LDS and PLC value for each pixel in an array of pixels corresponding to respective voxels in said ROI; and selectively displaying said arrays of LDS and PLC pixel values. Said inducing of shear waves can comprise inducing a multi-tone signal with randomized phases that produces a waveform with an approximately uniform envelope.

According to some embodiments, a method of imaging linear dispersion slope (LDS) and power law coefficient (PLC) values and shear wave attenuation (alpha) values on a pixel-by-pixel basis for an internal region of a subject comprises: concurrently inducing shear waves at respective different vibration frequencies in a region of interest (ROI) in the subject; measuring displacements as a function of time of respective voxels in said ROI in the presence of said induced shear waves; applying computer algorithms to said displacements and accounting for said vibration frequencies to calculate respective shear wave speeds in said ROI and to further calculate a respective LDS and PLC and alpha value for each pixel in an array of pixels corresponding to respective voxels in said ROI; and selectively displaying said arrays of LDS and PLC pixel values. Said calculating of alpha values can comprise calculating from real and imaginary parts of a complex autocorrelation function of said displacements.

BRIEF DESCRIPTION OF THE DRAWINGS

FIG. 5 comprises graphs illustrating: (a) SWS versus frequency plots for the CIRS breast; and (b) comparable plots for the viscoelastic phantom (b). The depth and lateral positions of the ROI center point are indicated above each plot. For these plots, mean and standard deviation values were extracted for the ROIs that have the '*' symbol in FIG. 3 and FIG. 4, respectively.

FIG. 8 comprises graphs illustrating: (a) SWS versus frequency plots for Patient #2's liver; and (b) comparable plots for Patient #3's liver. The depth and lateral positions of the ROI center point are indicated above each plot. For these plots, mean and standard deviation values were extracted for the ROIs that have the '*' symbol in FIG. 6 and FIG. 7, respectively.

FIG. 11 comprises graphs illustrating: (a) SWS versus frequency plots for Patient #4's breast; and (b) comparable plots for Patient #5's breast. The depth and lateral positions of the ROI center point are indicated above each plot. For these plots, mean and standard deviation values were extracted for the ROIs that have the '*' symbol in FIG. 9 and FIG. 10, respectively.

DETAILED DESCRIPTION

A detailed description of examples of preferred embodiments is provided below. While several embodiments are described, the new subject matter of this patent specification is not limited to any one embodiment or combination of embodiments described herein, but instead encompasses numerous alternatives, modifications, and equivalents. In addition, while numerous specific details are set forth in the following description in order to provide a thorough understanding, some embodiments can be practiced without some or all these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements.

Specific experiments with specific parameters are described below but the disclosed approach applies to other experimental conditions as well and is not limited to the specific parameters and conditions of the experiments described below. Any imaging system capable of measuring small displacements in tissues can be utilized in place of the ultrasound system described below, including optical and magnetic resonance systems.

Figure 1A:
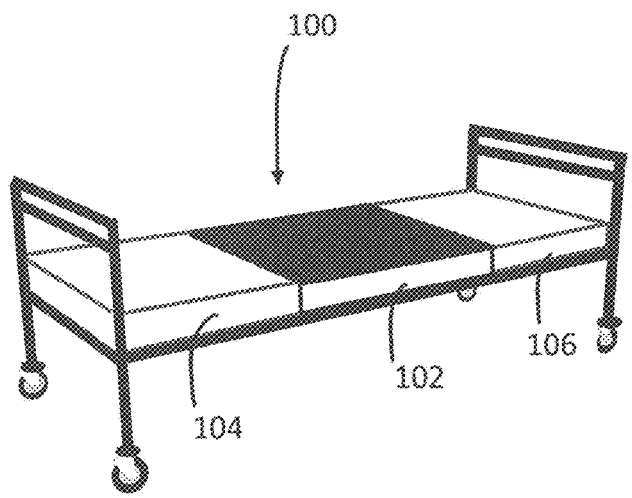
FIG. 1A illustrates a patient examination bed, with a region of active vibration drivers, for supporting a patient.

FIG. 1A illustrates a patient bed 100 that has an active central area 102 containing plural, integrated vibration sources, such as 4, 6, or more vibration sources. Preferably, for patient comfort the top surface of the active area 102 is flush with mattress portions 104 and 106. One example of patient table 100 is a portable trifold futon (70×60×10 cm$^3$) with multiple embedded vibration sources such as Quad Resonator Model E1718™, Elastance Imaging LLC, Columbus, Ohio, USA. The futon can be mounted to a standard hospital clinical bed as illustrated, to generate a desired reverberant shear wave field in the patient. In experiments described further below, vibration frequency ranged between 50-500 Hz (steps of 50 Hz) and 40-400 Hz (steps of 40 Hz) for use with C IRS phantoms and in liver experiments. In addition, a frequency range of 117-702 Hz (steps of 117 Hz) was used in the breast experiments. All frequencies, at the selected vibration frequency range, preferably are applied simultaneously in all the vibration sources for each experiment to thereby generate the desired reverberant shear wave field.

Figure 1B:
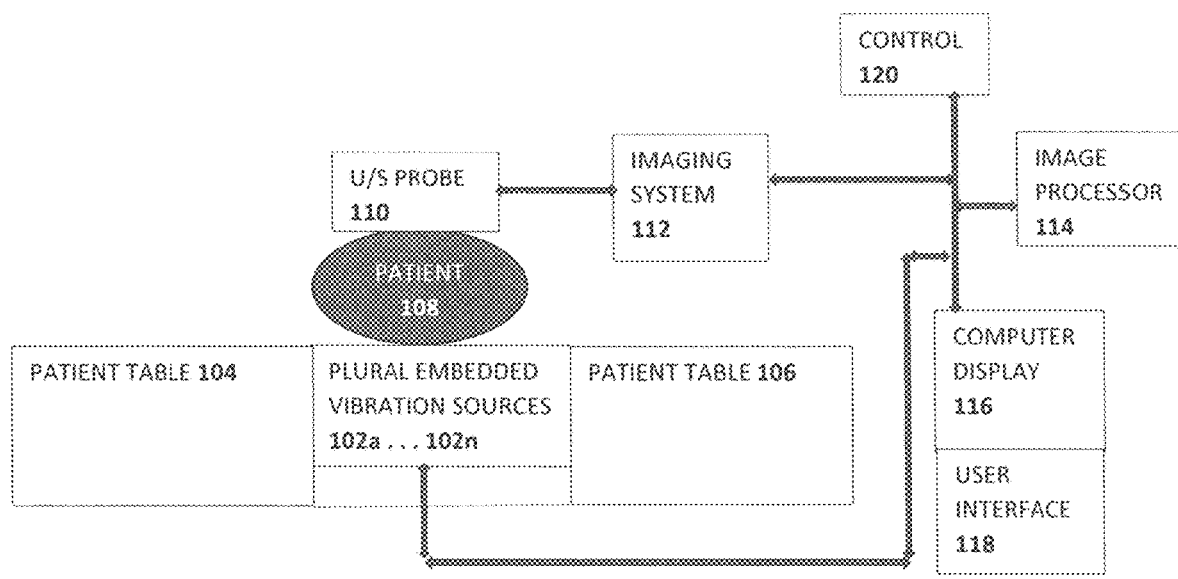
FIG. 1B illustrates an example of a system for imaging patients' internal tissue that carries out processes described below.

FIG. 1B illustrates an example of a system carrying out the processes described in detail further below. The system includes the active area 102 of patient table 100, with plural vibration sources 102a, 102b, 102n embedded therein, on which patient 108 is recumbent so that vibrations from active area 102 are induced in a volume or organ of interest in patient 108. Ultrasound transducer 110 acoustically couples to patient 108 to track motion of or in the organ or volume of interest that is subjected to shear waves due to action of vibration sources 102. In one example, a convex ultrasound probe 110 (model C4-2, ATL, Bothell, Wash., USA) was used to track induced displacement of liver tissue and in a viscoelastic phantom, and in another a linear ultrasound probe 110 (model L7-4, ATL, Bothell, Wash., USA) was used to track induced displacements in breast tissue and in a breast phantom. The center frequencies were 3 MHz and 5 MHz for the curved and linear probes, respectively. The sampling frequencies were 12 MHz and 20 MHz for the curved and linear probes, respectively. The tracking pulse repetition frequency (PRF) was set to 3600 Hz with a total acquisition time of 0.5 seconds. Transducer 110 is operatively coupled with an imaging system 112 that can be an ultrasound scanner such as Verasonics ultrasound system (Vantage-128™, Verasonics, Kirkland, Wash., USA). Alternatively, other imaging modalities can be used to track motion or displacement of particles or voxels in the volume of interest, such as MRI, OCT (Optical Coherence tomography), or other x-ray modalities that are capable of measuring or estimating motion in the presence to shear waves as a function of time. An image processor 114 can communicate with imaging system 112 to carry out some or all the processing described below, or all the processing can be done in imaging system 112. Computer display 116 is coupled with imaging system 112 and/or image processor 114 to display results such as those illustrated in FIGS. 2-11. User interface 118 such as keyboard, mouse, and/or touch screen facilitates control over desired functions. A control 120 is coupled with all the other illustrated elements to provide overall control and operation to carry out the processes that imaging system 112 and/or image processor 114 are programmed to carry out according to the examples described below.

Figure 1C:
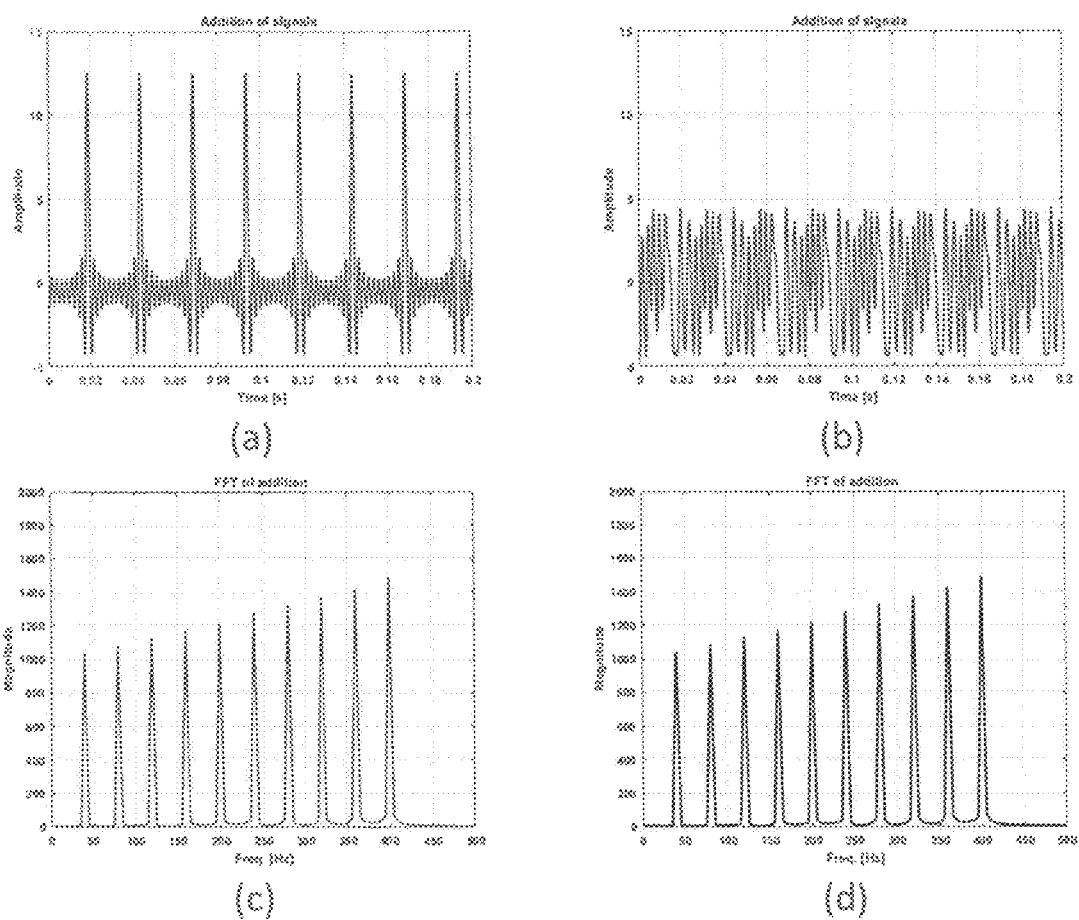
FIG. 1C shows a multi-tone vibration signal based on a superposition of 10 different frequencies (40 to 400 Hz in steps of 40 Hz) with phases multiple of $\pi/2$ and optimum random phases that avoid high periodic peaks.

Optimum random phase distribution for each vibration signal. FIG. 1C illustrates a randomized phase pattern that has been found to result in a superposition of multi-tones that does not have a sharp periodic peak but has a more uniform envelope. An optimization method can be used to find the phase distribution that minimizes or at least significantly reduces the magnitude of the superimposed waveform vibration signal by applying a Monte Carlo exhaustive search. This is useful for smoothing the envelope of the multi-tone signal and minimizing or reducing high peak voltages on the amplifier and the transducers. FIG. 1C illustrates a multi-tone vibration signal based on the superposition of 10 different frequencies (40 to 400 Hz in steps of 40 Hz). The amplitude of each single frequency vibration increases with frequency according to an empirical exponential function to compensate for attenuation at higher frequencies. In portion (a) of FIG. 1C, each frequency component contains a different phase shift multiple of $\pi/2$. As can be observed, the multi-tone signal has a sharp periodic peak with high peak voltages and demands high transient responses of an amplifier and transducers that produce vibration frequencies of the type described below, which should be minimized or at least kept low. Portion (b) of FIG. 1C illustrates a multi-tone signal with optimum random phases that smooths the magnitude or envelope of the vibration signal. Portions (c) and (d) of FIG. 1C illustrate Fourier transform analysis for the graphs of portions (a) and (b), respectively. The analysis illustrates the frequency composition of the superimpose signal with the exponential increment for the higher frequency components.

Noise reduction filtering. A filtering process similar to that used by Ormachea et al. (2018) was applied in the experiments described below. In this case each vibration frequency of the multi-frequency vibration range was processed using a low ($f_{li}$) and high ($f_{hi}$) cutoff frequencies of the finite impulse response (FIR) bandpass temporal filter. The cutoff frequencies were set at $f_{li}=(f_{vi}-10)$ Hz and $f_{hi}=(f_{vi}+10)$ Hz, where the subscript i indicates the corresponding i-th frequency of the multi-vibration frequency range. Additionally, the low ($k_{li}$) and high ($k_{hi}$) cutoff spatial frequencies (related to the wavenumber (k)) of the filter were set at $k_{li}=2\pi f_{vi}/c_h$ and $k_{hi}=2\pi f_{vi}/c_l$, where $c_l$ and $c_h$ are the minimum and maximum SWS limits and were set to 0.8 m/s, and 5 m/s for phantoms and liver experiments, respectively. For the breast experiments, $c_l$ and $c_h$ were set to 0.8 m/s, and 7 m/s, respectively.

Reverberant shear wave field and 2D shear wave speed estimator. The wavenumber and, subsequently, the SWS were estimated using the method described by Parker et al. (2017). The wavenumber was estimated by evaluating the second derivative of the autocorrelation function of the reverberant shear wave signal at the origin ($B_{vv}(0)$). This can be approximated by a finite difference. Thus:

$$|\hat{k}|^2 \cong C[\text{Re}\{B_{vv}(0)\} - \text{Re}\{B_{vv}(\Delta x)\}], \qquad (1)$$

where C is a constant equal to $10/(\Delta x^2 B_{vv}(0))$, and the $\Delta x$ lag and zero lag values of the real part of the autocorrelation at $\Delta t=0$ from some segment of data are used. Further detailed analysis of the reverberant shear wave field and SWS estimation are found in Parker et al. (2017).

The wavenumber and SWS can then be related using the equation:

$$c_s(\omega) = \frac{2\pi f_v}{k} = \frac{\omega}{k}, \quad (2)$$

(NB) where $c_s$ is the shear wave speed at a given vibration frequency and $\omega$ is the frequency in radians/sec.

2D linear dispersion slope and power law coefficient estimation. Shear wave phenomena are associated with harmonic and transient approaches. Harmonic schemes, including R-SWE, decompose a harmonic ensemble into their frequency contents. When these techniques estimate shear wave propagation around a specific frequency, the results can be classified as phase velocity. In Parker et al. (2018), it was shown that some viscoelastic phantoms and soft tissues exhibit a power law response. In these cases, the phase velocity can be written as:

$$c_s = c_1 \omega^\alpha \quad (3)$$

where $c_1$ is the phase velocity measured at $\omega=1$ rad/s, and $\alpha$ is the power law coefficient.

In practice, the relationship between SWS and frequency is evaluated over the vibration frequency range. Frequently the simplest measurement of dispersion is the linear slope ($dc_s/d\omega$). However, this parameter has been found in tissues to vary strongly as a function of frequency. Considering a power law media, a simplification results if one plots $c_s$ versus $\omega$ data on a log-log scale. In this case, the slope will be independent of frequency:

$$\frac{d(\log(c_s))}{d(\log(\omega))} = a, \quad (4)$$

In other words, the slope or dispersion as measured from a log-log plot of $c_s$ versus $\omega$ will be constant across different frequency bands, whereas the slope from a linear plot will vary with frequency. In the experiments described in this patent specification, multi-frequency data are analyzed for both the traditional linear (slope) dispersion and for power law dispersion by performing a linear regression fitting. This regression result is rejected if the goodness-of-fit metrics $R^2 < 0.7$.

Previous derivations and references (Parker et al., 2017; Ormachea et al., 2018) have treated reverberant shear wave fields in an elastic medium, meaning a tissue or organ with negligible losses or attenuation. A new approach described in this patent specification utilizes the discovery that for a viscoelastic biomaterial with shear wave attenuation $\alpha$ (Np/cm), a complex wavenumber can be introduced into the derivation to include the effects of attenuation. In that case, the autocorrelation function, obtained perpendicularly and parallel to the sensor in the axial direction (z-axis) respectively, of shear wave velocity within the reverberant field becomes $$B_{vv}[\Delta\varepsilon, \alpha, k] = \frac{4\pi^2(-(2\alpha z + ik\Delta\varepsilon)\cosh[2\alpha z + ik\Delta\varepsilon] + (1 + (2\alpha z + ik\Delta\varepsilon)^2)\sinh[2\alpha z + ik\Delta\varepsilon])}{(2\alpha z + ik\Delta\varepsilon)^3}, \quad (5)$$

$$B_{vv}[\Delta\varepsilon, \alpha, k] = \frac{2\pi^2((8\alpha z + 4ik\Delta\varepsilon)\cosh[2\alpha z + ik\Delta\varepsilon] - 4\sinh[2\alpha z + ik\Delta\varepsilon])}{(2\alpha z + ik\Delta\varepsilon)^3}, \quad (6)$$

and it is found that the real part of the autocorrelation is dominated by the real part of the wavenumber k, whereas the attenuation term a dominates the imaginary part of the autocorrelation. Thus, both the shear wave speed and the shear wave attenuation can be estimated from the real and imaginary parts of the complex autocorrelation functions, respectively. In cases where the multifrequency approach is utilized, and where attenuation is expected to be a function of frequency, the ratio of the imaginary parts of the autocorrelation function at two different frequencies can be used as an independent assessment of dispersion.

Thus, this new approach involves the estimation of shear wave speed and attenuation from calculating the real part and the imaginary part of the complex autocorrelation function and comparing the results to the theoretical value to obtain the best fit of the wavenumber and attenuation parameters.

Figure 2:
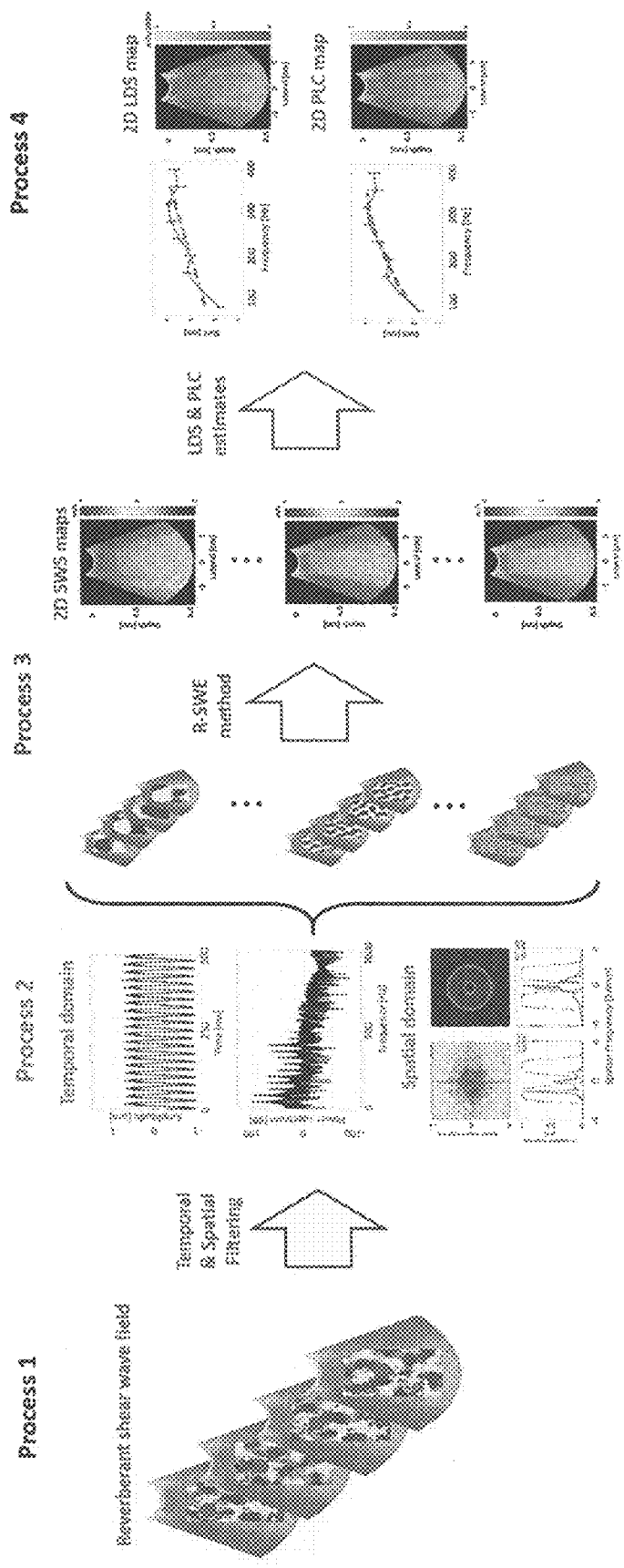
FIG. 2 illustrates a reverberant shear wave elastography (R-SWE) process to obtain 2D SWS maps for their corresponding vibration frequencies ($f_v$), two-dimensional (2D) linear dispersion slope (LDS) maps, and 2D power law coefficient (PLC) maps.

FIG. 2 summarizes a process to obtain 2D SWS maps for their corresponding $f_v$ (vibration frequency) using the R-SWE approach, the final 2D linear dispersion slope (LDS), and the 2D power law coefficient (PLC) maps. 'Process 1' shows snapshots from a movie of a typical R-SWE field using a multi-frequency range. Each snapshot comprises an array of pixels that represent values of induced displacement at a respective instant of time of respective particles or voxels in the tissue or phantom. Then, 'Process 2' illustrates the particle displacement in time and its corresponding frequency spectrum showing each fv applied in the material. Additionally, it illustrates the spatial frequency spectrum from a 2D spatial domain matrix, the 2D spatial bandpass noise reduction filter, and two different profiles at the lateral and axial axes. After filtering each $f_v$, 'Process 3' applied the R-SWE method to obtain the 2D SWS maps. The upper 4 maps in the left portion of 'Process 3' illustrate results for a lower frequency, the middle 4 snapshots illustrate results for a higher frequency, and the bottom 4 snapshots illustrate results for the highest frequency. The righthand column in 'Process 3" illustrates the SWS maps for the corresponding frequencies, where each pixel represents the SWS value of a respective voxel in the tissue or phantom. The rectangles in these 2D SWS maps represents a region of interest (ROI) used in the calculations. Finally, 'Process 4' takes the 2D SWS maps and their corresponding frequencies to calculate or estimate the LDS and the PLC. The corresponding 2D image is obtained by repeating the process at each pixel location. The upper image in 'Process 4' is a 2D LDS map where each pixel value is an estimate of the linear dispersion slope at a corresponding voxel in the volume of interest (the shaded central rectangle). The upper graph shows the SWS (shear wave speed) estimate as a function of vibration frequency. The lower image in 'Process 4' is a 2D PLC map where each pixel value is an estimate of the power law coefficient at a corresponding voxel in the volume of interest (the shaded central rectangle), and the lower graph also shows the SWS (shear wave speed) estimate as a function of vibration frequency. Notably, the upper and lower images are 2D maps that show a value of the respective parament on a pixel-by-pixel basis.

CIRS phantoms. The experiments described in this patent specification used a CIRS breast phantom (Model 059, Computerized Imaging Reference Systems, Norfolk, Va., USA) that has a size and shape to simulate a patient in the supine position; a homogeneous part (20-kPa nominal Young's modulus) from the background region was chosen to evaluate R-SWE. Then, a custom made CIRS (Serial No. 2095.1-1, Computerized Imaging Reference Systems) homogeneous viscoelastic phantom (6-kPa nominal Young's modulus) was chosen to evaluate R-SWE. The rectangularshaped phantom was protected by a case with openings that allowed contact with the external vibration sources at two lateral borders.

In vivo liver and breast patients. Five healthy volunteer patients were scanned to evaluate the feasibility of applying the R-SWE modality in in vivo experiments. One thin and two obese patients were scanned for the in vivo liver experiments. Two patients, one with a breast fibroadenoma and one with dense breast tissue, were scanned for breast experiments. During the experiments, the patients reclined supine on the custom bed.

Figure 3:
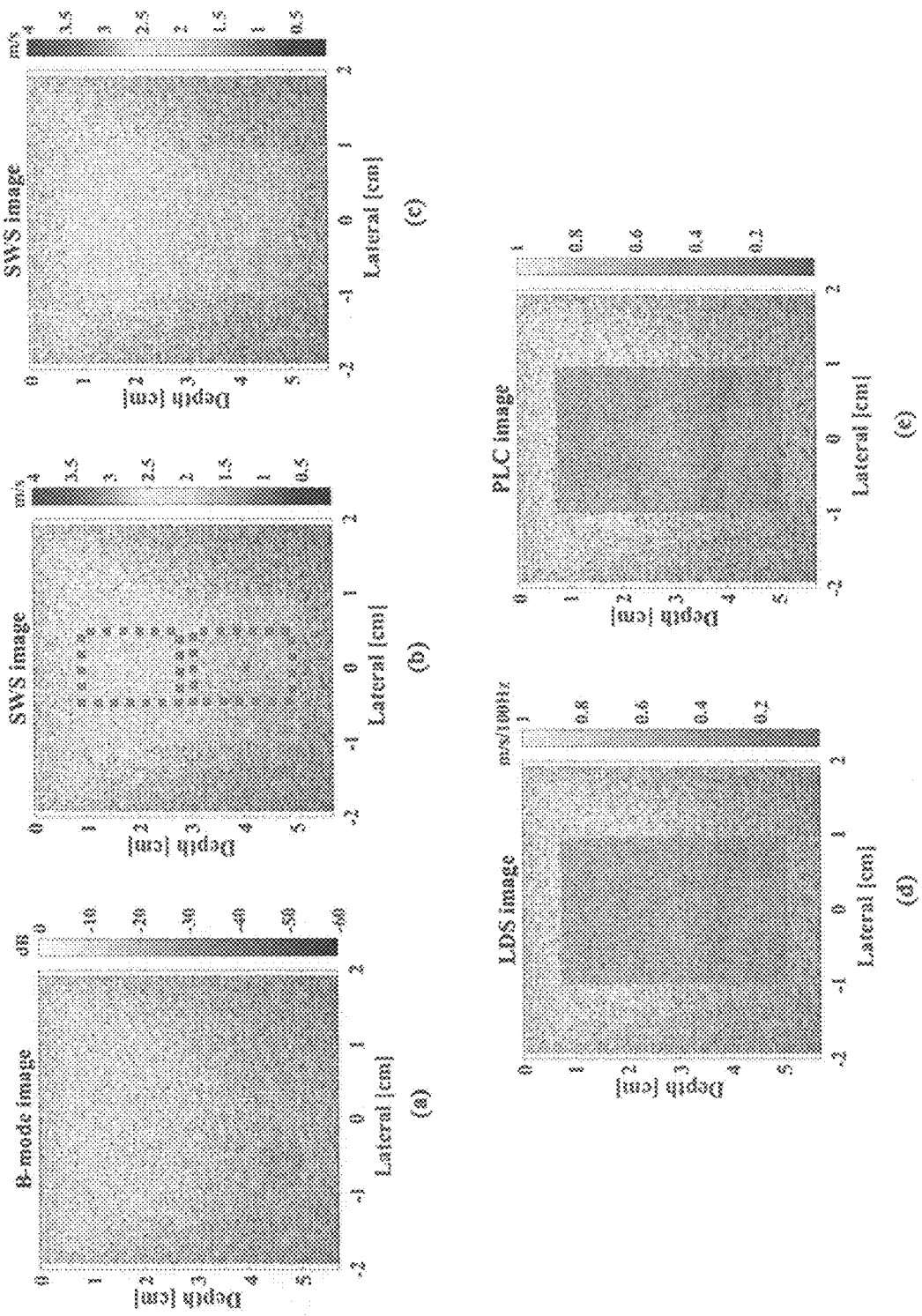
FIG. 3 comprises illustrations of: (a) B-mode images for a CIRS breast phantom; (b) and (c), SWS images, superimposed on their corresponding B-mode image, obtained with the R-SWE approach at two different vibration frequencies, 200 Hz and 300 Hz, respectively; and (d) and (e), linear dispersion slope and power law coefficient images using a 200-500 Hz frequency range. The dash line squares illustrate the selected regions of interest (ROIs) that are only shown in one image for reference purposes and are used to calculate mean and standard deviation values showed in Table 1 set out in the text further below. The '*' symbol illustrates the center point of one ROI that was used to plot dispersion curves in portion (a) of FIG. 5.

FIG. 3 illustrates results for SWS in a CIRS breast phantom. Portion (a) of FIG. 3 shows a B-Mode ultrasound image of the breast phantom. Portion (b) shows an SWS image superimposed on the B-Mode image of portion (a), where the SWS image was obtained at 200 Hz vibration frequency with the R-SWE and with two areas outlined in dotted lines within a rectangular region of interest (ROI). Portion (c) shows an SWS image of an ROI and is like portion (b) but was obtained at 300 Hz vibration frequency. Portion (d) shows an LDS image of the ROI, and portion (e) shows a PLC image of the ROI. For the LDS and PLC images in portions (d) and (e) in FIG. 3, the frequency range of 200-500 Hz was selected as it meets the established fitting rule ($R^2 > 0.7$). Subsequently, two region of interest (ROI) of 2×1 cm$^2$ were extracted at 1.8 cm and 4 cm depth for each image to obtain a reference mean SWS, LDS, and PLC and their standard deviations (SD). The dash line squares in portion (b) illustrate selected ROIs (only shown in one image for reference purposes) to calculate mean and standard deviation values showed in Table 1 below. The '*' symbol illustrates the center point of one ROI that was used to plot dispersion curves in portion (a) of FIG. 5.

Figure 4:
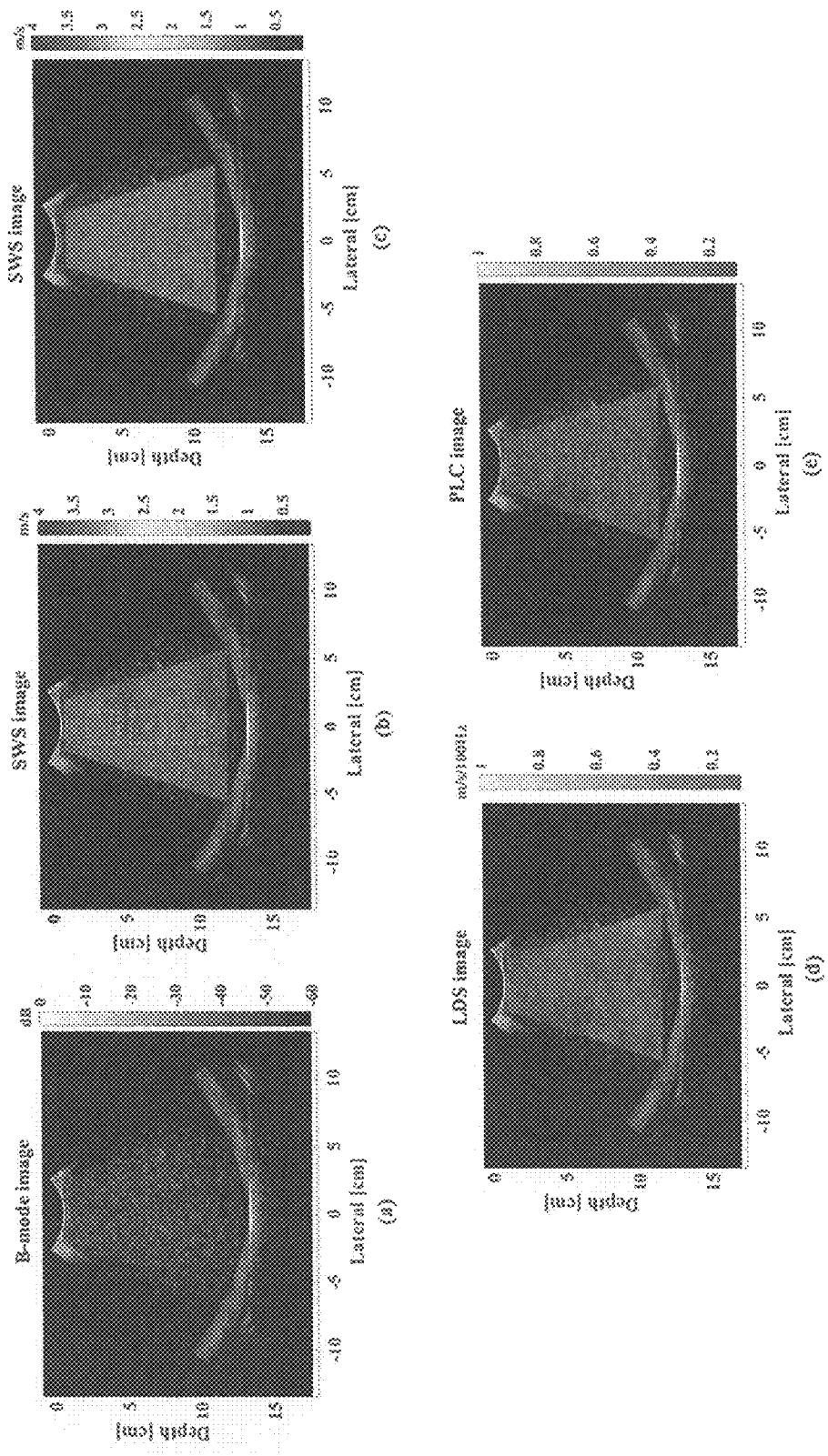
FIG. 4 comprises illustrations of: (a) B-mode images for a CIRS viscoelastic phantom; (b) and (c), SWS images, superimposed on their corresponding B-mode image, obtained with the R-SWE approach at two different vibration frequencies, 80 Hz and 200 Hz, respectively; and (d) and (e), linear dispersion slope and power law coefficient images using a 80-320 Hz frequency range. The dash line squares illustrate the selected ROIs (only show in one image for reference purposes) to calculate mean and standard deviation values showed in Table 1. The '*' symbol illustrates the center point of one ROI that was used to plot dispersion curves in portion (b) of FIG. 5.

FIG. 4 is like FIG. 3 but is for a CIRS viscoelastic phantom. FIG. 4 shows the SWS, LDS, and PLC maps superimposed on their corresponding B-mode image for the CIRS viscoelastic phantom. For LDS and PLC images, the frequency range of 80-320 Hz was selected as it meets the established fitting rule ($R^2 > 0.7$). For this case, three ROIs of 2×2 cm$^2$ size were selected at different positions, since the convex probe that was used for this phantom covers a bigger field of view, to obtain reference mean SWS, LDS, and PLC and their SD, at 4 cm, 6 cm, and 8 cm depth. As with FIG. 3, FIG. 4 shows: (a) a B-Mode ultrasound image, (b) an SWS image with outlined areas obtained at 80 Hz vibration frequency, (c) an SWS image obtained at 200 Hz in portion, and LDS and PLC images in portions (d) and (e) respectively, using an 80-320 Hz frequency range. The dash line squares illustrate the selected ROIs (only shown in one image for reference purposes) to calculate mean and standard deviation values shown in Table 1. The '*' symbol illustrates the center point of one ROI that was used to plot dispersion curves in portion (b) of FIG. 5.

FIG. 5 shows in portion (a) a reference plot of SWS as a function of frequency for the CIRS breast phantom, extracted from the ROIs with the '*' symbol at the center region of portions (b) in FIG. 3. Portion (b) is a reference plot of SWS as a function of frequency for the CIRS viscoelastic phantom, extracted from the ROIs with the '*' symbol at the center region of portions (b) in FIG. 4. As expected, the SWS remained nearly constant for the breast phantom since it is a nearly elastic material (LDS=0.10±0.02 m/s/100 Hz; PLC=0.18±0.11). On the other hand, the SWS increased with an increasing frequency for the viscoelastic phantom (LDS=0.42±0.02 m/s/100 Hz; PLC=0.34±0.03). Additionally, the goodness of the fit curve, represented by the $R^2$ value, is also reported for each LDS and PLC results in Table 1.

Figure 6:
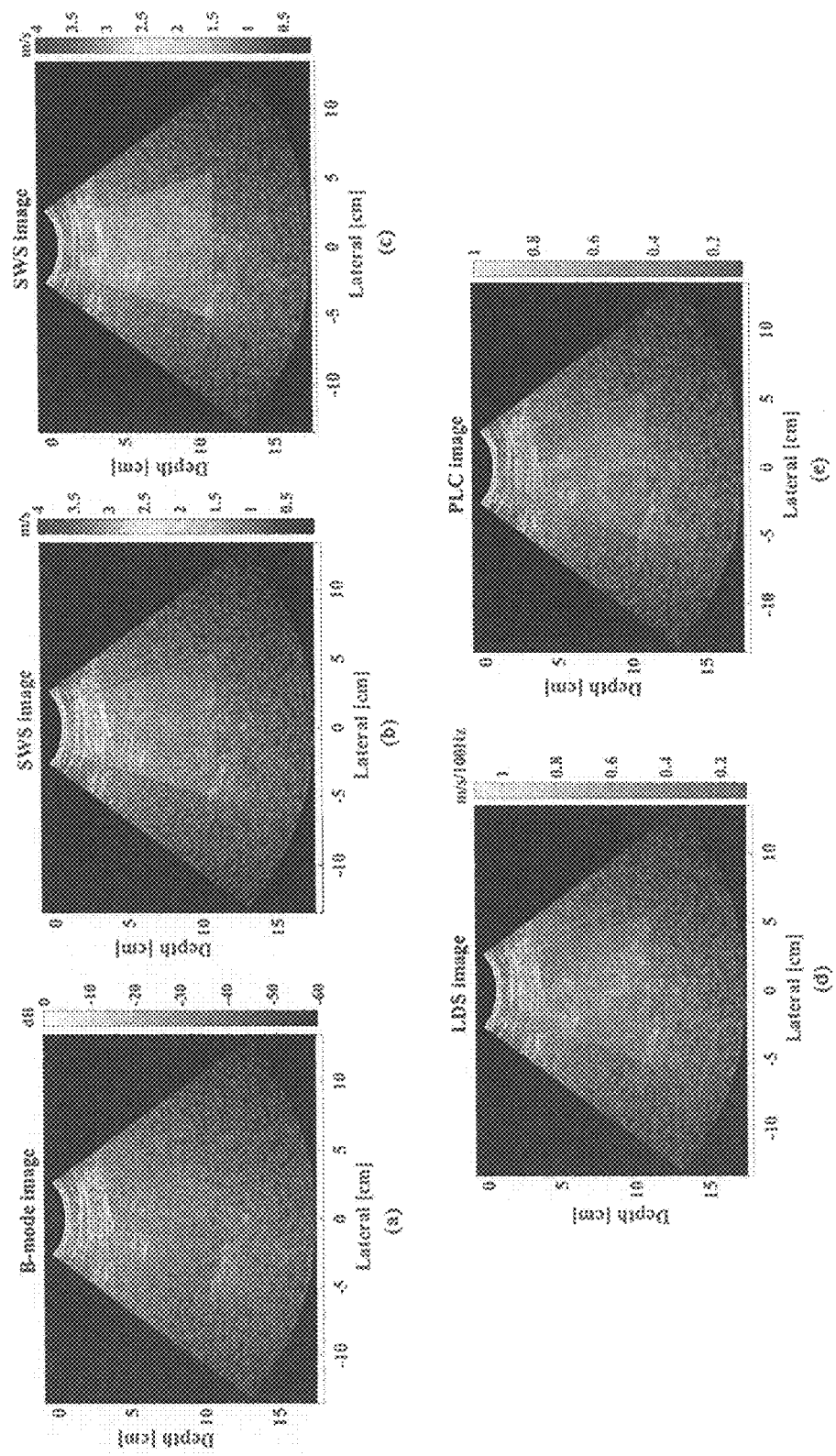
FIG. 6 comprises illustrations of: (a) B-mode images Patient #2 (liver obese case); (b) and (c), SWS images, superimposed on their corresponding B-mode image, obtained with the R-SWE approach at two different vibration frequencies, 80 Hz and 200 Hz, respectively; and (d) and (e), linear dispersion slope and power law coefficient images using a 80-320 Hz frequency range. The dash line squares illustrate the selected ROIs (only show in one image for reference purposes) to calculate mean and standard deviation values showed in Table 1. The '*' symbol illustrates the center point of one ROI that was used to plot dispersion curves in FIG. 8(a).
Figure 7:
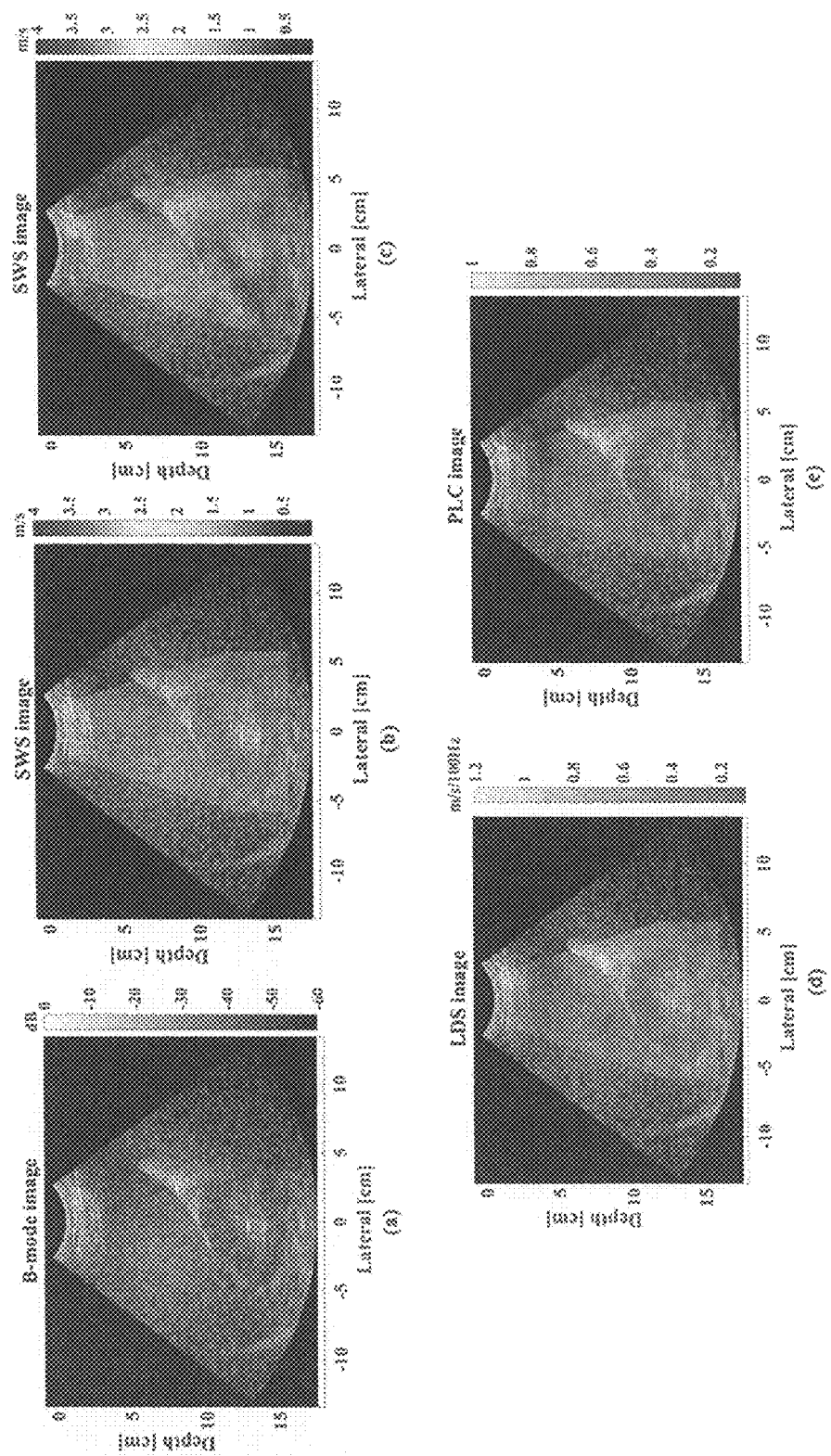
FIG. 7 comprises illustrations of: (a) B-mode images for Patient #3 (liver obese case); (b) and (c), SWS images, superimposed on their corresponding B-mode image, obtained with the R-SWE approach at two different vibration frequencies, 80 Hz and 200 Hz, respectively; and (d and e), linear dispersion slope and power law coefficient images using a 80-320 Hz frequency range. The dash line squares illustrate the selected ROIs (only show in one image for reference purposes) to calculate mean and standard deviation values showed in Table 1. The '*' symbol illustrates the center point of one ROI that was used to plot dispersion curves in FIG. 8(b).

In vivo liver elastography results. For the in vivo liver experiments, three ROIs of 2×2 cm$^2$ size were located at different positions to obtain a reference mean SWS, LDS, and PLC and their SD. FIGS. 6 and 7 show the different viscoelastic images for two respective obese patients (cases 2 and 3, respectively) and are like FIGS. 3 and 4 in arrangement of portions (a) through (e). For LDS and PLC images, the frequency range of 80-320 Hz was selected as it is a similar and comparable frequency range to the various liver studies that measured the linear dispersion (Parker et al., 2015) and it meets the established fitting rule ($R^2 > 0.7$). A distinction between fat/muscle and liver tissue were obtained for frequencies higher than 100 Hz for all cases. The liver is located 4-11 cm depth and 4-10 cm depth in FIG. 6 and FIG. 7, respectively. Thus, R-SWE was able to measure the viscoelastic properties of liver tissue in obese patients at deep regions. Additionally, it can be observed that the kidney was also measured in FIG. 7. For this case, a simple observation at 200 Hz shows a clearer distinction between the kidney cortex and the liver tissue. This may suggest that R-SWE might be able to measure the viscoelastic properties in kidney tissue.

FIG. 8 shows reference plots of SWS as a function of frequency, extracted from the ROIs with the '*' symbol at the center region, for both obese liver patients. Portion (a) is for obese patient case 2 and portion (b) is for obese patient case 3. Both patients show higher LDS and PLC results than the thin patient's liver and (see Table 1 for details). Additionally, the goodness of the fit curve, represented by the $R^2$ value, is also reported for each LDS and PLC results in Table 1.

Figure 9:
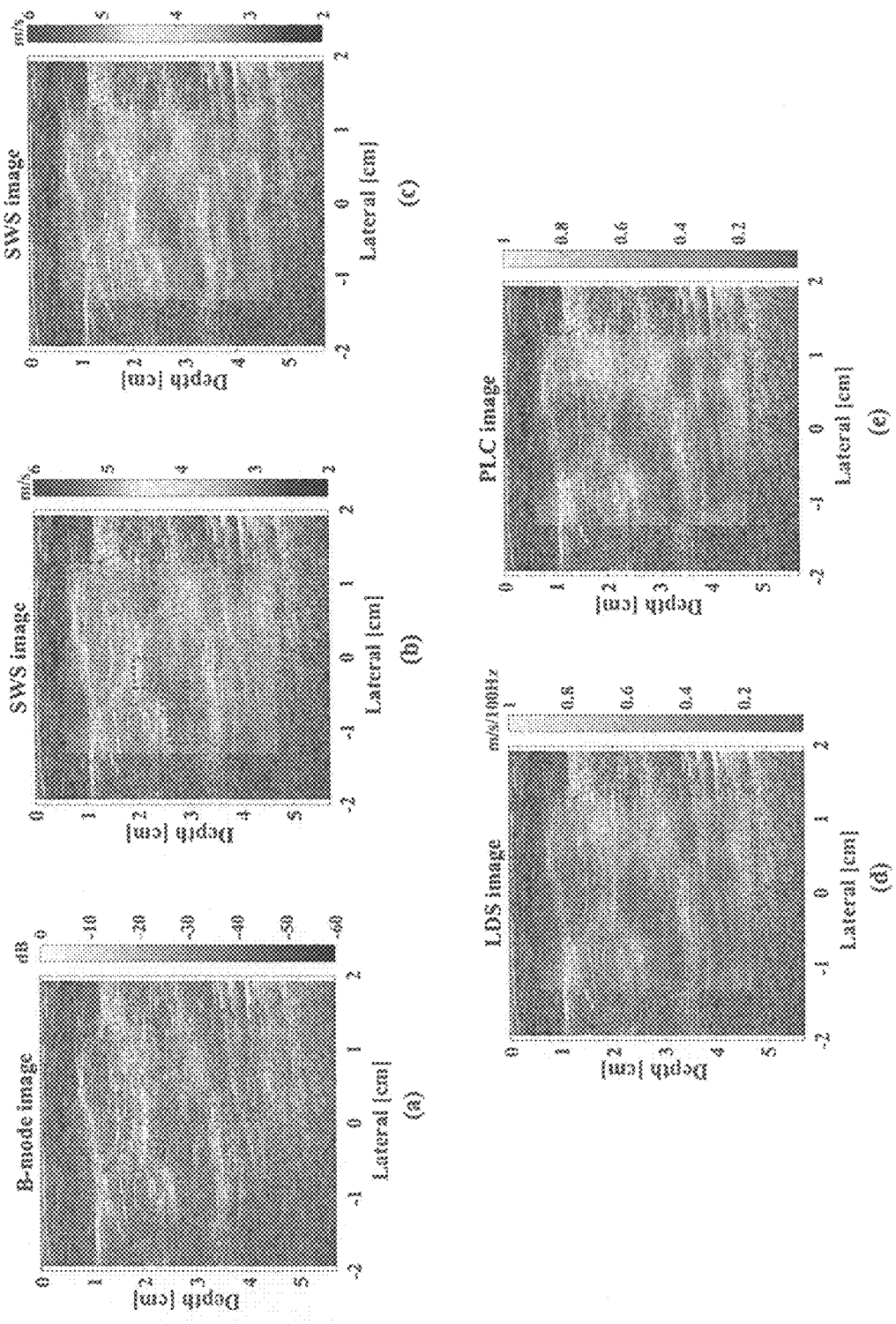
FIG. 9 comprises illustrations of: (a) B-mode images for Patient #4 (breast fibroadenoma case); (b) and (c), SWS images, superimposed on their corresponding B-mode image, obtained with the R-SWE approach at two different vibration frequencies, 585 Hz and 702 Hz, respectively; and (d) and (e), linear dispersion slope and power law coefficient images using a 468-702 Hz frequency range. The dash line squares illustrate the selected ROIs (only shown in one image for reference purposes) to calculate mean and standard deviation values showed in Table 1. The '*' symbol illustrates the center point of one ROI that was used to plot dispersion curves in FIG. 11(a).

In vivo breast elastography results. FIG. 9 shows a breast experiment with benign fibroadenoma. Portions (a) through (e) correspond to the respective portions of FIG. 3 but are for an in vivo breast experiment. The SWS maps of portions (b) and (c) illustrate the presence of the lesion that has a lower SWS than the surrounding tissue. Three ROIs of 0.5×0.5 cm$^2$ were selected to cover the fibroadenoma lesion to obtain the mean SWS, LDS, and PLC reference values. The SWS value was lower than benign masses reported in Barr et al. (2015). Portions (b) and (c) of FIG. 9 show results obtained with the R-SWE approach at two different vibration frequencies, 585 Hz and 702 Hz, respectively. Portions (d) and (e) of FIG. 9 show linear dispersion slope and power law coefficient images using a 468-702 Hz frequency range. The dash line squares illustrate the selected ROIs (only shown in one image for reference purposes) to calculate mean and standard deviation values showed in Table 1. The '*' symbol illustrates the center point of one ROI that was used to plot dispersion curves in portion (a) of FIG. 11.

Figure 10:
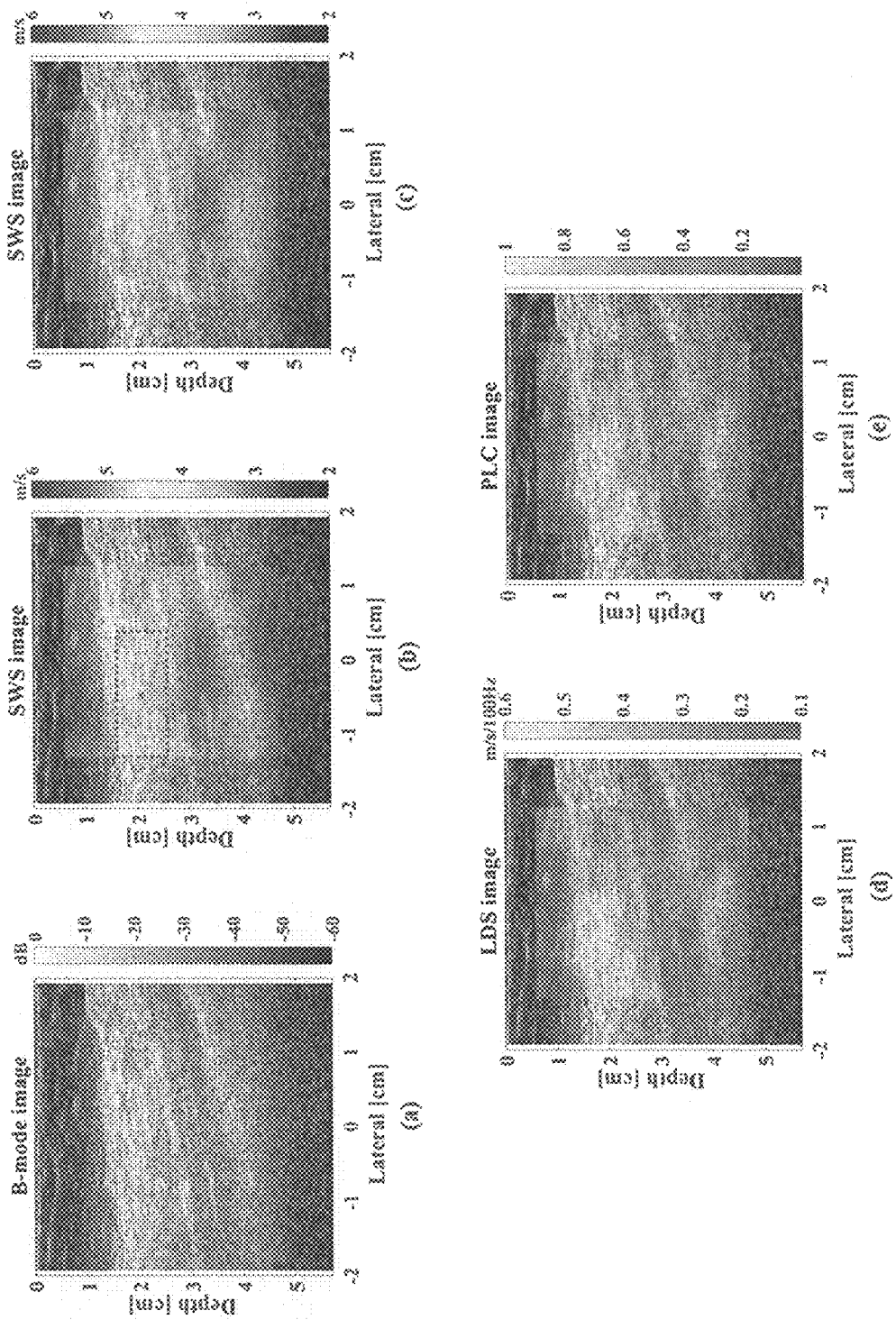
FIG. 10 comprises illustrations of: (a) B-mode images for Patient #5 (dense breast tissue case); (b) and (c), SWS images, superimposed on their corresponding B-mode image, obtained with the R-SWE approach at two different vibration frequencies, 585 Hz and 702 Hz, respectively; and (d) and (e), linear dispersion slope and power law coefficient images using a 468-702 Hz frequency range. The dash line square illustrates the selected ROI (only shown in one image for reference purposes) to calculate mean and standard deviation values showed in Table 1. The '*' symbol illustrates the center point of one ROI that was used to plot dispersion curves in FIG. 11(a).

FIG. 10 shows the viscoelastic results for a dense breast tissue experiment. An ROI of 1×2 cm$^2$ was selected to cover the dense breast tissue area and the mean SWS of 4.33±0.34 m/s and 3.77±0.09 m/s for the dense and fat regions were obtained, respectively. The arrangement of portions (a) through (e) is like in FIG. 3. The SWS images of portions (b) and (c) of FIG. 10 were obtained with the R-SWE approach at two different vibration frequencies, 585 Hz and 702 Hz, respectively, and the linear dispersion slope and power law coefficient images of portions (d) and (e) were obtained using a 468-702 Hz frequency range. The dash line square illustrates the selected ROI (only show in one image for reference purposes) to calculate mean and standard deviation values showed in Table 1. The '*' symbol illustrates the center point of one ROI that was used to plot dispersion curves in portion (a) of FIG. 11.

FIG. 11 shows reference plots of SWS as a function of frequency, extracted from the ROIs with the '*' symbol at the center region, for the breasts of FIGS. 9 and 10 respectively. For LDS and PLC images, the frequency range of 468-702 Hz was selected as SWS images showed better contrast difference between the fibroadenoma lesion/surrounding tissue, and fat/dense-breast-tissue regions at this vibration frequencies, and it meets the established fitting rule ($R^2 > 0.7$). Additionally, the goodness of the fit curve, represented by the $R^2$ value, is also reported for each LDS and PLC results in Table 1. The depth and lateral positions of the ROI center point are indicated above each plot. For these plots, mean and standard deviation values were extracted for the ROIs that have the '*' symbol in FIG. 9 and FIG. 10, respectively.

The table below is a summary of viscoelastic properties measured or estimated according to the processes described in this patent specification.

fat/muscle layer and liver tissue was obtained at vibration frequencies higher than 100 Hz. To the inventors' knowledge, this is the first study that attempted to measure the liver viscoelastic properties in obese patients using continuous vibration frequencies up to 400 Hz at deep areas. Thus, the R-SWE approach may be able to overcome one of the main clinical limitations of applying elastography to the liver: the ability to obtain a SWS image in obese cases (Ferraioli et al., 2015) throughout the liver volume. For each patient, the mean SWS obtained at 200 Hz is presented in Table 1. The reported SWS is lower than 2.5 m/s; this value is mentioned because it illustrates a threshold to differentiate low fibrosis (<F2) from high fibrosis (>F3) at 200 Hz in Nightingale et al. (2015). In that sense, the results shown in this patent specification are reasonable since none of the scanned patients have a confirmed high score. Additionally, a low LDS value was obtained for the thin liver patient compared to the two obese patients (see Table 1). The LDS results were obtained using a frequency range of 80-320 Hz and agree with other studies for patients with low fibrosis (<F2).

TABLE 1

Summary of viscoelastic material properties in different media

| Media | fv [Hz] | sws [m/s] | LDS [m/s/100 Hz] | PLC | fv range [Hz] | $R^2$ for LDS | $R^2$ for PLC |
|---|---|---|---|---|---|---|---|
| Breast phantom | 200 | 2.15 ± 0.11 | 0.10 ± 0.02 | 0.18 ± 0.11 | 200-500 | 0.77 ± 0.14 | 0.73 ± 0.12 |
| Viscoelastic phantom | 200 | 1.88 ± 0.38 | 0.42 ± 0.02 | 0.34 ± 0.03 | 80-320 | 0.73 ± 0.05 | 0.71 ± 0.07 |
| Patient #1, liver thin case | 200 | 1.99 ± 0.19 | 0.28 ± 0.14 | 0.23 ± 0.10 | 80-320 | 0.92 ± 0.05 | 0.90 ± 0.07 |
| Patient #2, liver obese case | 200 | 2.29 ± 0.37 | 0.49 ± 0.17 | 0.44 ± 0.09 | 80-320 | 0.82 ± 0.14 | 0.80 ± 0.12 |
| Patient #3, liver obese case | 200 | 2.38 ± 0.20 | 0.54 ± 0.19 | 0.43 ± 0.04 | 80-320 | 0.75 ± 0.14 | 0.72 ± 0.17 |
| Patient #4, breast fibroadenoma case | 702 | 3.71 ± 0.29 | 0.29 ± 0.04 | 0.54 ± 0.32 | 468-702 | 0.72 ± 0.09 | 0.75 ± 0.11 |
| Patient #5, dense breast tissue case | 702 | 4.33 ± 0.34 | 0.48 ± 0.15 | 0.58 ± 0.21 | 468-702 | 0.96 ± 0.12 | 0.95 ± 0.17 |

Discussion. For the experiments described in this patent specification, a multi-frequency 3D (e.g. 2D space+time) reverberant shear wave field was created in different media. For all of them, SWS and dispersion maps were obtained using the R-SWE approach. The new dispersion images enabled better characterization of the viscoelastic properties of different tissues in a complete 2D field of view. The results in the CIRS phantoms illustrated the capability of R-SWE to differentiate between elastic and viscoelastic media by measuring the SWS frequency dependence. Additionally, the homogeneity in the SWS and LDS maps is consistent with the homogeneous composition for each material. It is shown that the dispersion is lower for the almost purely elastic breast phantom (i.e. 0.10±0.02 m/s/100 Hz) than the viscoelastic phantom (i.e. 0.42±0.02 m/s/100 Hz).

For the in vivo liver scans, the R-SWE approach was applied in one thin and two obese patients. It is notable that this technique was able to measure the viscoelastic properties at deep areas (~16 cm depth) in obese patients. As can be seen in FIGS. 6 and 7, a clear difference between the Linear dispersion values were approximately between 0.1 and 0.6 m/s/100 Hz using a frequency range of 0-400 Hz in Nightingale et al. (2015). Furthermore, (Defficux et al., 2009; Muller et al., 2009) found a LDS value equals to 0.36±0.06 m/s/100 Hz in in vivo healthy human volunteers using frequencies ranges of 40-450 Hz and 60-390 Hz, respectively, which is slightly higher to the LDS value obtained in the thin liver patient in this patent specification. The results obtained herein and comparisons of these results with other liver studies illustrate that the R-SWE approach can measure the viscoelastic properties in in vivo liver tissue, in obese patients and at deep areas.

For the in vivo breast scans, a patient with a fibroadenoma and a patient with a dense breast tissue were imaged. In both cases, higher vibration frequencies, up to 702 Hz, were applied because breast tissue stiffness is usually higher than liver tissue (Barr et al., 2015; Ferraioli et al., 2015) and shorter shear wavelengths could be obtained to improve the spatial resolution of the R-SWE approach to detect lesions. For the fibroadenoma patient, a mean SWS of 3.71±0.29 m/s was obtained at 702 Hz inside the lesion. Following the "aggressive rule" proposed by Barr et al. (2015), the lesion could be considered as a "low stiffness lesion". Similarly, according to Elseedawy et al. (2016), this breast mass could be considered as a soft fibroadenoma because it meets the following characteristics: the lesion stiffness (<4.08 m/s), the patient's age (<50 years), and the lesion diameter size (<1.5 cm). In the second breast experiment, the dense breast tissue case, a mean SWS of 4.33*0.34 m/s was obtained within the dense tissue area at 702 Hz. This SWS value indicates that it is a benign mass because it is lower than 5.2 m/s (Barr et al., 2015; Chang et al., 2011). Another parameter that can be included to classify this mass as a benign lesion is the mass/fat ratio proposed by Cebi Olgun et al. (2014). In that study, the mass/fat ratio was measured in 115 patients with different breast lesions and it was found that a ratio lower than 4.6 helps to differentiate benign and malignant breast lesions. In the results in this patent specification, the dense tissue/fat ratio was equal to 1.32 (56.25 kPa/42.64 kPa) using the mean SWS values of 4.33 m/s and 3.77 m/s for the dense breast tissue and fat regions, respectively. An analysis of the LDS results for breast tissue and what these numbers could mean diagnostically is currently uncertain due to the lack of dispersion studies in breast using SWE. Kumar et al. (2018) analyzed the phase SWS with respect to frequency in normal, benign, and malignant breast tissues in 43 patients. They found significant differences between the shear viscosity of benign and malignant lesions: higher shear viscosity values were reported for malignant lesions than benign lesions. One hypothesis therefore is that benign lesions should have lower dispersion values. In our study, LDS for the fibroadenoma case was less than for the dense breast tissue, but both cases were within the range of the LDS values for the liver patients experiments this patent specification describes, and furthermore, both breast cases represent benign lesions. The processes described herein can be used to determine "low" and "high" thresholds for dispersion in breast tissue, as well as other clinically relevant factors such as (a) the frequency range to measure the LDS (in this preliminary study it was higher than that used for the liver cases), (b) the surrounding tissue properties (fat, dense, mixed), and (c) age effects. It is encouraging that the LDS images herein show additional contrast between the fibroadenoma lesion and surrounding tissue as well as between the dense breast tissue and the fat region. Applying the R-SWE approach could obtain a better characterization of breast lesions using both SWS and LDS images.

The other parameter reported in this patent specification is the PLC. The results for the CIRS phantoms show a clear difference between the almost purely elastic (0.18±0.11) and the viscoelastic (0.34±0.03) phantoms. In Parker et al. (2018), a PLC equals to 0.48 was obtained for the same viscoelastic phantom but using a discrete frequency range of 80-220 Hz. The mean PLC results for the in vivo livers also show a difference between the thin liver (0.25±0.04) and the obese liver cases (One Patient: 0.44±0.09; Another Patient: 0.43±0.04) indicating that the PLC may be an additional parameter that could help differentiate the tissue viscoelastic properties. Other studies measured the PLC in in vivo healthy livers too. Parker et al. (2018) reported a PLC equals to 0.47 from discrete frequencies of 100-240 Hz and Zhang and Holm (2016) showed a table summarizing different PLC values reported in the literature: the reported PLC values were 0.18 from 25-62.5 Hz using Magnetic Resonance Elastography (MRE) and 0.5 from 75-600 Hz using Shear Wave Spectroscopy. For our in vivo breast results, the mean PLC values also differ from the fibroadenoma (0.54±0.32) and the dense breast tissue (0.58±0.21). Zhang and Holm (2016) reported a PLC of 0.85 for malignant breast tumors using MRE. On the other hand, Sinkus et al. (2007) obtained a PLC of 0.84 for a healthy breast volunteer using MRE. Both MRE studies used similar frequency ranges, 60-100 Hz and 65-100 Hz, respectively. To compare the PLC values from the study reported herein with those from Zhang and Holm (2016) and Sinkus et al. (2007), we need to divide their reported PLC by a factor of 2, since they reported the Shear Modulus power law while this patent specification report the SWS power law. The theories that interrelate these different approaches can be found in Parker et al. (2018).

As can be observed, in cases where a power law model has been explicitly applied, estimates of the power law parameter are wide-ranging and thus it might be determined what PLC can add to clinical differentiation of tissues based on better characterization of their viscoelasticity properties.

Finally, a practical issue for clinicians concerns the time required for data acquisition and processing of the estimator images, particularly for ultrasound systems that are intended for real time operation. In the study examples reported in this patent specification, the SWS and dispersion results were obtained post-processing rather than as a real time operation. However, high frame rate ultrasound scanning and high complexity shear wave algorithms are already implemented on a number of ultrasound systems, so the limiting factor may be the time required to acquire a satisfactory estimate of the reverberant autocorrelation function. For this study, the total acquisition time was 0.5 s to track at least 10 periods for the lower frequency component of the multi-frequency vibration range. Of course, less could be utilized depending on noise and unwanted tissue motion, however this illustration points to the use of reverberant elastography frame rates that are perceived as real time.

The results of the experiments reported above demonstrate that reverberant shear wave fields can be produced in deep tissues from external sources, up to at least 400 Hz in obese patients' livers and over 700 Hz in breast tissue. The use of multi-frequency tones simultaneously applied enables a rapid collection of shear wave response and then the analysis of SWS and dispersion at discrete frequencies. The dispersion can be analyzed as a slope (change in SWS with change in frequency), or as a power law coefficient consistent with a more advanced framework of tissue rheology. These dispersion estimates are then obtained over the entire ROI and used to form dispersion images. These may provide additional information and image contrast in cases where lesions or pathologies demonstrate an altered viscoelastic response, and therefore an altered dispersion parameter, compared with normal tissue. The techniques described in this patent specification can be used to define the practical upper limits to shear wave frequencies applied to the breast or liver within our framework, and the range of normal dispersions expected within a healthy population.

Although the foregoing has been described in some detail for purposes of clarity, it will be apparent that certain changes and modifications may be made without departing from the principles thereof. It should be noted that there are many alternative ways of implementing both the processes and apparatuses described herein.

Accordingly, the present embodiments are to be considered as illustrative and not restrictive, and the body of work described herein is not to be limited to the details given herein, which may be modified within the scope and equivalents of the appended claims.

REFERENCES

Amador C, Urban M W, Chen S and Greenleaf J F 2011 Shearwave dispersion ultrasound vibrometry (SDUV) on swine kidney IEEE Trans Ultrason Ferroelectr Freq Control 58 2608-19

Barr R G 2014 Elastography in clinical practice Radiol Clin North Am 52 1145-62

Barr R G, Nakashima K, Amy D, Cosgrove D. Farrokh A, Schafer F, Bamber J C, Castera L, Choi B I, Chou Y H, Dietrich C F, Ding H, Ferraioli G, Filice C, Friedrich-Rust M, Hall T J, Nightingale K R, Palmeri M L, Shiina T, Suzuki S, Sporea I, Wilson S and Kudo M 2015 WFUMB guidelines and recommendations for clinical use of ultrasound elastography: Part 2: breast Ultrasound Med Biol 41 1148-60

Barry C T, Hah Z, Partin A, Mooney R A, Chuang K H, Augustine A, Almudevar A, Cao W, Rubens D J and Parker K J 2014 Mouse liver dispersion for the diagnosis of early-stage Fatty liver disease: a 70-sample study Ultrasound Med Biol 40 704-13

Barry C T, Hazard C, Hah Z, Cheng G, Partin A, Mooney R A, Chuang K H, Cao W, Rubens D J and Parker K J 2015 Shear wave dispersion in lean versus steatotic rat livers J Ultrasound Med 34 1123-9

Callé S, Simon E, Dumoux M-C, Perrotin F and Remenieras J-P 2018 Shear wave velocity dispersion analysis in placenta using 2-D transient elastography Journal of Applied Physics 123 234902

çebi Olgun D, Korkmazer B, KIIIç F, Dikici A S, Velidedeoğlu M, Aydoğan F, Kantarci F and YIlmaz M H 2014 Use of shear wave elastography to differentiate benign and malignant breast lesions Diagnostic and interventional radiology (Ankara, Turkey) 20 239-44

Chang J M, Moon W K, Cho N, Yi A, Koo H R, Han W, Noh D Y, Moon H G and Kim S J 2011 Clinical application of shear wave elastography (SWE) in the diagnosis of benign and malignant breast diseases Breast Cancer Res Treat 129 89-97

Deffieux T, Montaldo G, Tanter M and Fink M 2009 Shear wave spectroscopy for in vivo quantification of human soft tissues visco-elasticity IEEE Trans Med Imaging 28 313-22

Elseedawy M, Whelehan P, Vinnicombe S, Thomson K and Evans A 2016 Factors influencing the stiffness of fibroadenomas at shear wave elastography Clin Radiol 71 92-5

Ferraioli G, Filice C, Castera L, Choi B I, Sporea I, Wilson S R, Cosgrove D, Dietrich C F, Amy D. Bamber J C, Barr R, Chou Y H, Ding H, Farrokh A, Friedrich-Rust M, Hall T J, Nakashima K, Nightingale K R, Palmeri M L, Schafer F, Shiina T, Suzuki S and Kudo M 2015 WFUMB guidelines and recommendations for clinical use of ultrasound elastography: Part 3: liver Ultrasound Med Biol 41 1161-79

Hudert C A, Tzschatzsch H, Guo J, Rudolph B, Blaker H, Loddenkemper C, Luck W, Muller H P, Baumgart D C, Hamm B, Braun J, Holzhutter H G, Wiegand S and Sack I 2018 US Time-Harmonic Elastography: Detection of Liver Fibrosis in Adolescents with Extreme Obesity with Nonalcoholic Fatty Liver Disease Radiology 288 99-106

Kumar V, Denis M, Gregory A, Bayat M, Mehrmohammadi M. Fazzio R, Fatemi M and Alizad A 2018 Viscoelastic parameters as discriminators of breast masses: Initial human study results PLoS One 13 e0205717

Loupas T, Powers J T and Gill R W 1995 An axial velocity estimator for ultrasound blood flow imaging, based on a full evaluation of the Doppler equation by means of a two-dimensional autocorrelation approach IEEE Transactions on Ultrasonics, Ferroelectrics, and Frequency Control 42 672-88

Muller M, Gennisson J L, Defficux T, Tanter M and Fink M 2009 Quantitative viscoelasticity mapping of human liver using supersonic shear imaging: preliminary in vivo feasibility study Ultrasound Med Biol 35 219-29

Nightingale K R, Rouze N C, Rosenzweig S J, Wang M H, Abdelmalek M F. Guy C D and Palmeri M L 2015 Derivation and analysis of viscoelastic properties in human liver: impact of frequency on fibrosis and steatosis staging IEEE Trans Ultrason Ferroelectr Freq Control 62 165-75

Ormachea J, Castaneda B and Parker K J 2018 Shear Wave Speed Estimation Using Reverberant Shear Wave Fields: Implementation and Feasibility Studies Ultrasound Med Biol 44 963-77

Ormachea, J., Castaneda, B., and Parker, K. J. (2018). "Shear wave speed estimation using reverberant shear wave fields: implementation and feasibility studies," Ultrasound Med Biol, doi.org/10.1016/j.ultrasmedbio.2018.1001.1001.

Palmeri M, Nightingale K, Fielding S, Rouze N, Yufeng D, Lynch T, Chen S, Song P, Urban M, Xie H, Wear K, Garra B, Milkowski A, Rosenzweig S, Carson P, Barr R, Shamdasani V, Macdonald M, Wang M, Guenette G, Miyajima Y, Okamura Y, Dhyani M, Samir A, Hah Z, McLaughlin G, Gee A, Chen Y, Napolitano D, McAleavey S, Obuchowski N and Hall T 2015 IEEE International Ultrasonics Symposium (IUS), 21-24 Oct. 2015 2015), vol. Series) pp 1-4

Parker K J, Doyley M M and Rubens D J 2010 Imaging the elastic properties of tissue: the 20 year perspective Phys Med Biol 56 R1-R29

Parker, K. J., Ormachea, J., Zvietcovich, F., and Castaneda, B. (2017). "Reverberant shear wave fields and estimation of tissue properties," Phys Med Biol 62, 1046-1061.

Parker K J, Ormachea J and Hah Z 2018 Group versus Phase Velocity of Shear Waves in Soft Tissues Ultrason Imaging 40 343-56

Parker K J, Ormachea J, McAleavey S A, Wood R W, Carroll-Nellenback J J and Miller R K 2016 Shear wave dispersion behaviors of soft, vascularized tissues from the microchannel flow model Phys Med Biol 61 4890-903

Parker K J, Ormachea J, Zvietcovich F and Castaneda B 2017 Reverberant shear wave fields and estimation of tissue properties Phys Med Biol 62 1046-61

Parker K J, Partin A and Rubens D J 2015 What Do We Know About Shear Wave Dispersion in Normal and Steatotic Livers? Ultrasound in Medicine & Biology 41 1481-7

Rouze N C, Deng Y, Trutna C A. Palmeri M L and Nightingale K R 2018 Characterization of Viscoelastic Materials Using Group Shear Wave Speeds IEEE Trans Ultrason Ferroelectr Freq Control 65 780-94

Shiina T, Nightingale K R, Palmeri M L, Hall T J, Bamber J C, Barr R G, Castera L, Choi B I, Chou Y H, Cosgrove D, Dietrich C F, Ding H, Amy D, Farrokh A, Ferraioli G, Filice C, Friedrich-Rust M, Nakashima K, Schafer F, Sporea I, Suzuki S, Wilson S and Kudo M 2015 WFUMB guidelines and recommendations for clinical use of ultrasound elastography: Part 1: basic principles and terminology Ultrasound Med Biol 41 1126-47

Simon E G, Calle S, Perrotin F and Remenieras J P 2018 Measurement of shear wave speed dispersion in the placenta by transient elastography: A preliminary ex vivo study PLoS One 13 e0194309

Sinkus R, Siegmann K, Xydeas T, Tanter M, Claussen C and Fink M 2007 MR elastography of breast lesions: understanding the solid/liquid duality can improve the specificity of contrast-enhanced MR mammography Magn Reson Med 58 1135-44

Tanter M, Bercoff J, Athanasiou A, Deffieux T, Gennisson J L, Montaldo G, Muller M, Tardivon A and Fink M 2008 Quantitative assessment of breast lesion viscoelasticity: initial clinical results using supersonic shear imaging Ultrasound Med Biol 34 1373-86

Tzschatzsch H, Ipek-Ugay S, Trong M N, Guo J, Eggers J, Gentz E, Fischer T, Schultz M, Braun J and Sack I 2015 Multifrequency time-harmonic elastography for the measurement of liver viscoelasticity in large tissue windows Ultrasound Med Biol 41 724-33

Urban M W, Chen J and Ehman R L 2017 IEEE International Ultrasonics Symposium (IUS), 6-9 Sep. 2017 2017), vol. Series) pp 1-4

Zhang W and Holm S 2016 Estimation of shear modulus in media with power law characteristics Ultrasonics 64 170-6

Zvietcovich F, Rolland J P, Meemon P and Parker K International Tissue Elasticity Conference, (Avignon, France, 2018), vol. Series)

What is claimed is:

1. A system for estimating and displaying a dispersion slope on a pixel-by-pixel basis for a corresponding internal tissue of a mammal, comprising:
    a source of shear waves propagating in multiple directions, said source being configured to concurrently induce shear waves at respective different vibration frequencies in a region of interest (ROI) in the mammal;
    an imaging system measuring displacement as a function of time of respective voxels in said ROI in the presence of said induced shear waves;
    a computer processor configured to apply computer algorithms to said displacements and account for said vibration frequencies to calculate respective shear wave speeds in said ROI and to further calculate a viscoelastic dispersion slope for each pixel in an array of pixels corresponding to respective voxels in said ROI;
    and a computer display configured to selectively display the dispersion slope.

2. The system of claim 1, in which said processor is further configured to account in said computer algorithms for effects of attenuation (alpha) of said shear waves as they propagate in said region of interest (ROI).

3. The system of claim 2, in which said to calculating further comprises calculating a viscoelastic dispersion slope for each of said pixels and said displaying comprises displaying an array of said dispersion slope values.

4. The system of claim 1, in which said source of shear waves comprises a patient bed with plural sources of vibration frequencies embedded in an active region of said bed, wherein said plural sources are configured to vibrate concurrently.

5. The system of claim 1, in which said imaging system comprises an ultrasound scanner and an imaging ultrasound transducer.

6. The system of claim 5, in which said ultrasound scanner and transducer are configured to measure said displacements to a depth in the patient of at least 10 cm.

7. The system of claim 6, in which said ultrasound scanner and transducer are configured to measure said displacement in a patient's liver.

8. The system of claim 1, in which said imaging system is configured to measure said displacement in a patient's breast.

9. The system of claim 1, in which said imaging system comprises an OCT (Optical Coherence Tomography) scanner.

10. The system of claim 1, in which said source is configured to step said vibration frequencies in selected steps within a selected range of frequencies.

11. A system for estimating and displaying a dispersion slope on a pixel-by-pixel basis for a corresponding internal tissue of a mammal, comprising:
    a source of shear waves propagating in multiple directions, said source being configured to concurrently induce shear waves at respective different vibration frequencies and perform a Monte Carlo search for a phase distribution that minimizes the magnitude of a superimposed waveform vibration signal in a mammal;
    an imaging system measuring displacement as a function of time of respective voxels in the presence of said induced shear waves;
    a computer processor configured to apply computer algorithms to said displacements and account for said vibration frequencies to calculate respective shear wave speeds and to further calculate a viscoelastic dispersion slope for each pixel in an array of pixels corresponding to respective voxels;
    and a computer display configured to selectively display at least one of said arrays of linear dispersion slope (LDS) and power law coefficient (PLC) pixel values, in which said source of shear waves comprises a generator of a multi-tone signal with optimized phases that produces a waveform with an approximately uniform envelope.

12. The system of claim 11, in which said processor is further configured to account in said computer algorithms for effects of attenuation (alpha) of said shear waves as they propagate in an region of interest (ROI) of said mammal.

13. A system for estimating and displaying shear wave attenuation (alpha) values on a pixel-by-pixel basis for an internal tissue of a mammal, comprising:
    a source of a plurality of shear waves configured to concurrently induce shear waves at respective different vibration frequencies and perform a Monte Carlo search for a phase distribution that minimizes the magnitude of a superimposed waveform vibration signal in a mammal;
    an imaging system measuring displacements as a function of time of respective voxels in the presence of said induced shear waves;
    a computer processor configured to apply computer algorithms to said displacements to calculate respective shear wave speeds in and to further calculate a respective alpha value for each pixel in an array of pixels corresponding to respective voxels; and
    a computer display configured to selectively display an array of pixel values that correspond to said voxels and reflect said alpha values,
    in which said source of shear waves comprises a generator of a multi-tone signal with optimized phases that produces a waveform with an approximately uniform envelope.

14. The system of claim 13, in which said to calculating further comprises calculating a linear dispersion slope (LDS) value for each of said pixels and said displaying comprises displaying an array of said LDS values.

15. The system of claim 13, in which said to calculating further comprises calculating a power law coefficient (PLC) value for each of said pixels and said displaying comprises displaying an array of said PLC values.

16. A system for estimating and displaying a dispersion slope on a pixel-by-pixel basis for a corresponding internal tissue of a mammal, comprising:
- a source of shear waves propagating in multiple directions, said source being configured to concurrently induce shear waves at respective different vibration frequencies and optimized phases in a mammal;
- an imaging system measuring displacement as a function of time of respective voxels in said region of interest (ROI) in the presence of said induced shear waves;
- a computer processor configured to apply computer algorithms to said displacements and account for said vibration frequencies to calculate respective shear wave speeds and to further calculate a viscoelastic dispersion slope for each pixel in an array of pixels corresponding to respective voxels; and
- a computer display configured to selectively display at least one of said arrays of linear dispersion slope (LDS) and power law coefficient (PLC) pixel values,
- in which said source of shear waves comprises a generator of a multi-tone signal with optimized phases that produces a waveform with an approximately uniform envelope.

17. The system of claim 16, in which said processor is further configured to account in said computer algorithms for effects of attenuation (alpha) of said shear waves as they propagate in an region of interest (ROI) of the mammal.

18. A system for estimating and displaying shear wave attenuation (alpha) values on a pixel-by-pixel basis for an internal tissue of a mammal, comprising:
- a source of a plurality of shear waves configured to concurrently induce shear waves at respective different vibration frequencies and optimized phases in a mammal;
- an imaging system measuring displacements as a function of time of respective voxels in said region of interest (ROI) in the presence of said induced shear waves;
- a computer processor configured to apply computer algorithms to said displacements to calculate respective shear wave speeds in said ROI and to further calculate a respective alpha value for each pixel in an array of pixels corresponding to respective voxels; and
- a computer display configured to selectively display an array of pixel values that correspond to said voxels and reflect said alpha values,
- in which said source of shear waves comprises a generator of a multi-tone signal with optimized phases that produces a waveform with an approximately uniform envelope.

19. The system of claim 18, in which said to calculating further comprises calculating a linear dispersion slope (LDS) value for each of said pixels and said displaying comprises displaying an array of said LDS values.

20. The system of claim 18, in which said to calculating further comprises calculating a power law coefficient (PLC) value for each of said pixels and said displaying comprises displaying an array of said PLC values.

* * * * *